United States Patent [19]
Clement

[11] Patent Number: 5,797,907
[45] Date of Patent: Aug. 25, 1998

[54] ELECTROCAUTERY CUTTER

[75] Inventor: Thomas P. Clement, Bloomington, Ind.

[73] Assignee: Mectra Labs, Inc., Bloomfield, Ind.

[21] Appl. No.: 573,180

[22] Filed: Dec. 15, 1995

Related U.S. Application Data

[63] Continuation-in-part of Ser. No. 60,423, May 11, 1993, Pat. No. 5,505,210, which is a continuation-in-part of Ser. No. 956,601, Oct. 5, 1992, Pat. No. 5,335,671, which is a continuation-in-part of Ser. No. 830,580, Feb. 4, 1992, Pat. No. 5,409,013, which is a continuation-in-part of Ser. No. 580,945, Sep. 11, 1990, abandoned, which is a continuation-in-part of Ser. No. 432,084, Nov. 6, 1989, Pat. No. 5,019,054.

[51] Int. Cl.$^6$ .................................................. A61B 17/39
[52] U.S. Cl. ................................................ 606/49; 606/45
[58] Field of Search ................................. 128/749, 751–754; 606/42, 45, 46, 49

[56] References Cited

U.S. PATENT DOCUMENTS

| | | |
|---|---|---|
| 628,907 | 7/1899 | Hart . |
| 786,215 | 3/1905 | Hepnar . |
| 811,111 | 1/1906 | Wegefarth . |
| 1,585,934 | 5/1926 | Muir . |
| 1,658,754 | 2/1928 | Wood . |
| 2,437,329 | 3/1948 | Moore . |

(List continued on next page.)

FOREIGN PATENT DOCUMENTS

| | | |
|---|---|---|
| 0350291 | 5/1989 | European Pat. Off. . |
| 2332743 | 6/1977 | France . |
| 3528656 | 7/1986 | Germany . |
| 4120329 | 1/1992 | Germany . |
| 991478 | 5/1965 | United Kingdom . |
| 8103125 | 11/1981 | WIPO . |

OTHER PUBLICATIONS

K. Semm, "Pelviscopy–Operative Guidelines", Kiel, Germany 1988, pp. 53–54.

Pentax Precision Instrument Corp., "Gastrofiberscope", Surgical Products, Mar. 1990, vol. 9, No. 6, p. 13.

(List continued on next page.)

*Primary Examiner*—Max Hidenburg
*Attorney, Agent, or Firm*—Barnes & Thornburg

[57] ABSTRACT

A handheld electrocautery cutter is provided for suction, removal of body tissues and electrocauterization of tissue in a patient. The electrocautery cutter includes a distal end, a rigid cannula, a movable cutter, a cutter, a valve, a valve actuator, an electrical switch, and an electrical actuator. The rigid cannula defines a cannula interior and the cannula includes a proximal end and a distal end. The distal end of the cannula is insertible and positionable in a patient's body and the cannula defines a cannula opening adjacent the distal end to permit access to the cannula interior for capture of body tissue in the cannula interior. The movable cutter cuts tissue entering the cannula opening and the cutter actuator moves the cutter. The valve is connected to the cannula to control suction flow from the cannula interior and the valve actuator actuates the valve. The electrical switch is linked to the cannula to control mono-polar electrocautery current flowing from adjacent the distal end of the electrocautery cutter to the patient and the electrical actuator activates the electrical switch. The cannula and valve are integrated into a rigid structure to be held in a user's hand such that movement of the rigidly coupled cannula and valve by a user's hand allows the distal end of the cannula to be accurately positioned at a specific location in the patient's body. The cutter actuator, valve actuator, and electrical actuator are operable by a hand of the user as it moves the rigidly coupled valve and cannula to accurately position the distal end of the cannula in the patient's body.

41 Claims, 10 Drawing Sheets

U.S. PATENT DOCUMENTS

| | | |
|---|---|---|
| 2,708,437 | 5/1955 | Hutchins . |
| 2,715,899 | 8/1955 | MacLean . |
| 2,812,765 | 11/1957 | Tofflemire . |
| 2,888,928 | 6/1959 | Seiger ................................. 606/49 |
| 3,012,752 | 12/1961 | Buck . |
| 3,048,192 | 8/1962 | Murphy, Jr. . |
| 3,081,770 | 3/1963 | Hunter . |
| 3,109,426 | 11/1963 | Noonan et al. . |
| 3,157,201 | 11/1964 | Littmann . |
| 3,173,414 | 3/1965 | Guillant . |
| 3,368,734 | 2/1968 | Banko . |
| 3,434,691 | 3/1969 | Hamilton . |
| 3,467,082 | 9/1969 | Gilbert . |
| 3,682,177 | 8/1972 | Ames et al. . |
| 3,735,751 | 5/1973 | Katz . |
| 3,783,900 | 1/1974 | Waldbillig . |
| 3,788,602 | 1/1974 | Kitzie . |
| 3,794,032 | 2/1974 | Derouineau . |
| 3,833,000 | 9/1974 | Bridgman . |
| 3,834,372 | 9/1974 | Turney . |
| 3,837,345 | 9/1974 | Matar . |
| 3,853,127 | 12/1974 | Spademan . |
| 3,902,498 | 9/1975 | Niederer . |
| 3,957,082 | 5/1976 | Fuson et al. . |
| 3,994,287 | 11/1976 | Turp et al. . |
| 3,995,619 | 12/1976 | Glatzer . |
| 4,011,869 | 3/1977 | Seiler, Jr. . |
| 4,016,881 | 4/1977 | Rioux et al. . |
| 4,037,599 | 7/1977 | Raulerson . |
| 4,043,322 | 8/1977 | Robinson . |
| 4,073,297 | 2/1978 | Kopp . |
| 4,079,737 | 3/1978 | Miller . |
| 4,099,529 | 7/1978 | Peyman . |
| 4,111,207 | 9/1978 | Seiler, Jr. . |
| 4,173,328 | 11/1979 | Karbo . |
| 4,177,814 | 12/1979 | Knepshield et al. . |
| 4,198,959 | 4/1980 | Knepshield et al. . |
| 4,210,146 | 7/1980 | Banko . |
| 4,230,128 | 10/1980 | Aramayo . |
| 4,240,411 | 12/1980 | Hosono . |
| 4,261,357 | 4/1981 | Kontos . |
| 4,280,498 | 7/1981 | Jensen . |
| 4,282,873 | 8/1981 | Roth . |
| 4,282,884 | 8/1981 | Boebel . |
| 4,299,217 | 11/1981 | Sagae et al. . |
| 4,314,560 | 2/1982 | Helfgott et al. . |
| 4,314,586 | 2/1982 | Folkman . |
| 4,379,458 | 4/1983 | Bauer et al. . |
| 4,397,355 | 8/1983 | Doblar et al. . |
| 4,400,168 | 8/1983 | Buechel et al. . |
| 4,414,974 | 11/1983 | Dotson et al. . |
| 4,430,081 | 2/1984 | Timmermans . |
| 4,443,220 | 4/1984 | Hauer et al. . |
| 4,444,184 | 4/1984 | Oretorp . |
| 4,445,517 | 5/1984 | Feild . |
| 4,468,216 | 8/1984 | Muto . |
| 4,491,132 | 1/1985 | Aikins . |
| 4,512,344 | 4/1985 | Barber . |
| 4,519,385 | 5/1985 | Atkinson et al. . |
| 4,531,935 | 7/1985 | Berryessa . |
| 4,540,156 | 9/1985 | Cross . |
| 4,552,146 | 11/1985 | Jensen et al. . |
| 4,553,957 | 11/1985 | Williams et al. . |
| 4,553,964 | 11/1985 | Saski . |
| 4,566,480 | 1/1986 | Parham . |
| 4,568,332 | 2/1986 | Shippert . |
| 4,577,629 | 3/1986 | Martinez . |
| 4,581,014 | 4/1986 | Millerd et al. . |
| 4,589,414 | 5/1986 | Yoshida et al. . |
| 4,593,717 | 6/1986 | Levasseur . |
| 4,595,005 | 6/1986 | Jinotti . |
| 4,642,090 | 2/1987 | Utrata . |
| 4,642,097 | 2/1987 | Siposs . |
| 4,643,197 | 2/1987 | Greene et al. . |
| 4,644,951 | 2/1987 | Bays . |
| 4,645,496 | 2/1987 | Oscarsson . |
| 4,648,868 | 3/1987 | Hardwick et al. . |
| 4,651,753 | 3/1987 | Lifton . |
| 4,654,027 | 3/1987 | Dragan et al. . |
| 4,657,018 | 4/1987 | Hakky ................................. 606/49 |
| 4,662,871 | 5/1987 | Rafelson . |
| 4,667,927 | 5/1987 | Oscarsson . |
| 4,674,500 | 6/1987 | DeSatnick . |
| 4,676,242 | 6/1987 | Doi . |
| 4,681,123 | 7/1987 | Valtchev . |
| 4,690,672 | 9/1987 | Veltrup . |
| 4,692,140 | 9/1987 | Olson . |
| 4,702,260 | 10/1987 | Wang . |
| 4,708,147 | 11/1987 | Haaga . |
| 4,715,360 | 12/1987 | Akui et al. . |
| 4,735,606 | 4/1988 | Davison . |
| 4,758,235 | 7/1988 | Tu . |
| 4,793,359 | 12/1988 | Sharrow . |
| 4,807,666 | 2/1989 | Morse . |
| 4,808,155 | 2/1989 | Mahurkar . |
| 4,810,244 | 3/1989 | Allen . |
| 4,881,550 | 11/1989 | Kothe . |
| 4,900,300 | 2/1990 | Lee . |
| 4,911,202 | 3/1990 | Nelson . |
| 4,924,851 | 5/1990 | Ognier et al. ................................. 128/4 |
| 4,925,450 | 5/1990 | Imonti et al. . |
| 4,932,957 | 6/1990 | Zwick . |
| 4,958,621 | 9/1990 | Topel et al. . |
| 4,966,551 | 10/1990 | Betush . |
| 4,994,067 | 2/1991 | Summers . |
| 4,994,079 | 2/1991 | Genese et al. . |
| 5,019,035 | 5/1991 | Missirlian et al. . |
| 5,019,054 | 5/1991 | Clement et al. . |
| 5,053,044 | 10/1991 | Mueller et al. . |
| 5,078,688 | 1/1992 | Lobodzinski et al. . |
| 5,106,364 | 4/1992 | Hayafuji et al. . |
| 5,195,958 | 3/1993 | Phillips ................................. 604/33 |
| 5,197,963 | 3/1993 | Parins ................................. 606/46 |
| 5,273,524 | 12/1993 | Fox et al. . |
| 5,275,609 | 1/1994 | Pingleton et al. . |
| 5,335,671 | 8/1994 | Clement . |
| 5,348,555 | 9/1994 | Zinnanti ................................. 606/49 |
| 5,409,013 | 4/1995 | Clement . |
| 5,447,494 | 9/1995 | Dorsey, III ................................. 604/43 |
| 5,449,357 | 9/1995 | Zinnanti ................................. 606/49 |

OTHER PUBLICATIONS

Storz, "Laparoscopic Cholescystectomy for the General Surgeon—Its Time has Come", Surgical Products, May 1990, vol. 9, No. 6, p. 13.

Pentax Precision Instrument Corp., "GI Fiberscopes", Surgical Products, May 1990, vol. 9, No. 6, p. 13.

Healthco International Handbook, 1990, p. 116.

Storz The World of Endoscopy, Semm Instruments for Operative Pelviscopy, 4th Edition, Mar. 1987, pp. 1–4.

Richard Wolf cat. pg. and sketch/admitted prior art Jan. 1992.

American Surgical Instruments, Inc., "Nexhat–Dorsey Disposable Hydro–Dissection Trumpet Valve," 3 Sheets, Mar. 19, 1990.

Richard Wolf, "The Complete Endoscopy Manufacturer", Surgical Products, May 1990, vol. 9, p. 20.

Johnson & Johnson Medical Inc., "CIDEX is safe for scopes. Don't take our word for it." Surgical Products, May 1990, vol. 6, No. 9, p. 25.

Pentax®, "Pentax ® PNEII Bronchofiberscopes", Surgical Products, May 1990, vol. 9, No. 6, p. 44.

Pentax Precision Instrument Corp., "Therapeutic Gastrofiberscope with Water Jet", Sep. 1990, vol. 10, No. 1, p. 39.

EndoDynamics, Inc., "Aspiration Device", Surgical Products, Nov. 1990, vol. 10, p. 30.

"Irrigation/Aspiration Probe", Surgical Products, Sep. 1990, vol. 10, No. 11, p. 28.

Cabot Medical, "Laparoscopic Cholecystectomy From the Company Who Knows Laparoscopy", Surgical Products, Jan. 1991, vol. 20, No. 3, p. 4.

Olympus, "The Olympus Laparoscopic Cholecystectomy System: Resolution for Gallstones, with the leader in High--Resolution Optics", Surgical Products, Jan. 1990, vol. 10, No. 3, p. 8.

Apple Medical, "Hunt/Reich Secondary Cannula", Surgical Products, May 1991, vol. 10, No. 7, p. 5.

Baxter Healthcare Corp., "Infusion Pump", Surgical Products, Jun. 1991, vol. 10, No. 8, p. 32.

Core Dynamics TM Inc., "Disposable Trocar with Reusable Cannula", Surgical Products, Jun. 1991, vol. 10, No. 8, p. 4.

Dexide catalog page and sketch 1991.

Halkey Roberts catalog 1990 3 pages.

Cabot Medical, "Suction/Irrigation Probe", Surgical Products, Nov. 1990, vol. 10, No. 11, p. 29.

Megadyne®—Surgical Laparoscopy & Endoscopy, vol. 3, No. 4, p. 2, 1993 Raven Press.

Nezhat–Dorsey—Journal of Laparoendoscopic Surgery, vol. 4, No. 1, Feb. 1994, Inside front cover page ISSN: 1052–3901.

Cabot—The Journal of the American Association fo Gynecologic Laparoscopists, Nov., 1993, vol. 1, No. 1,

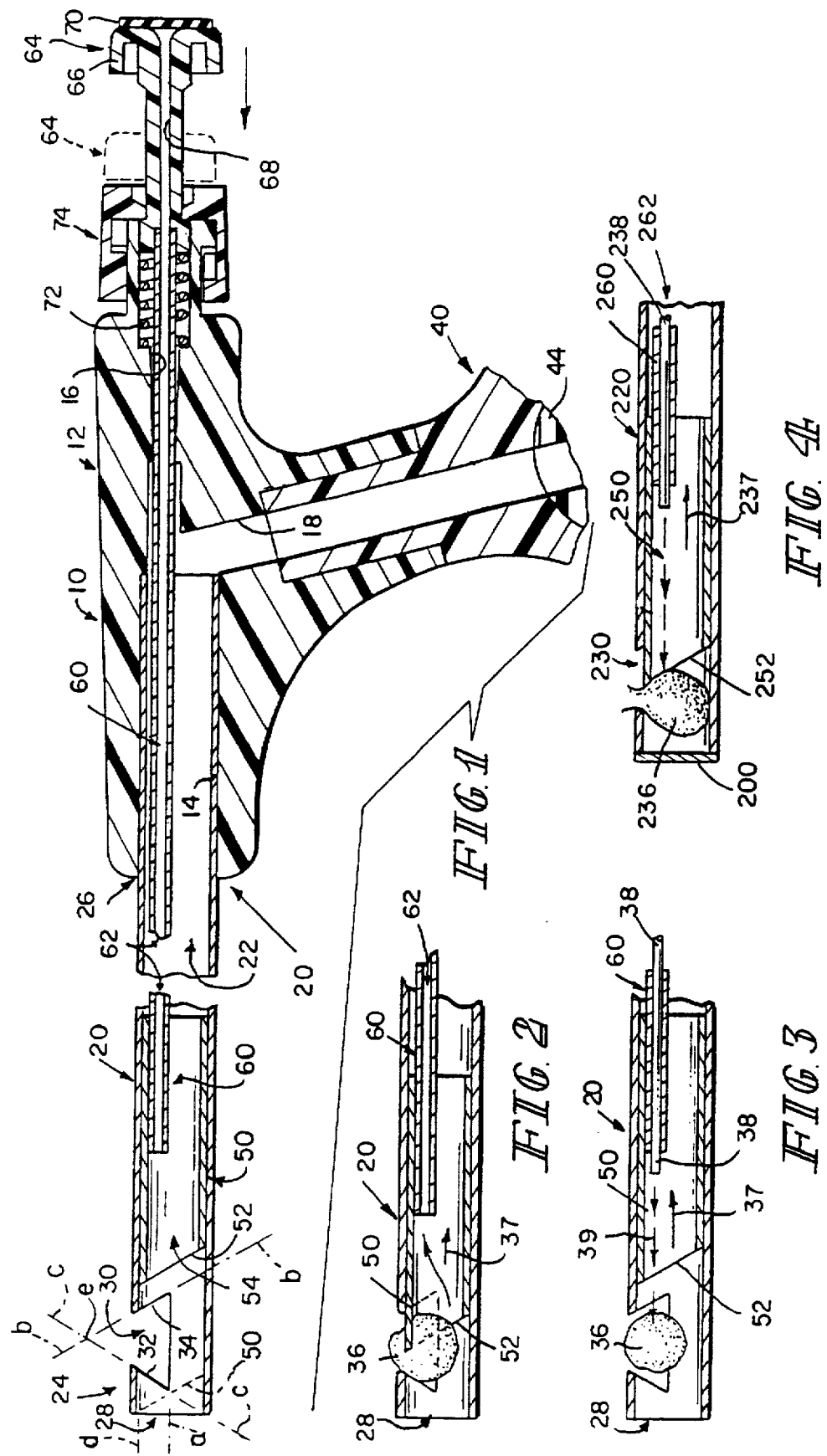

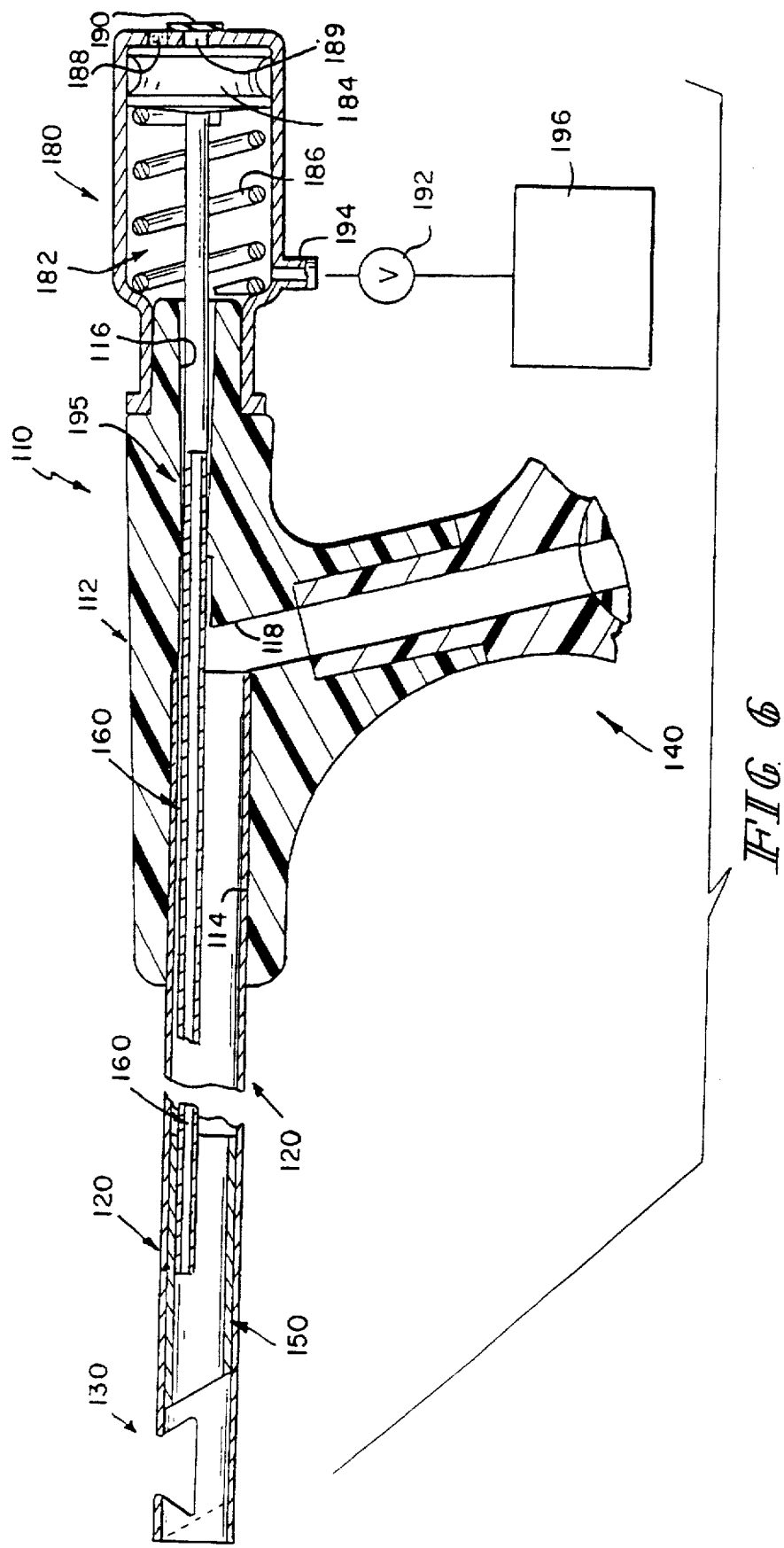

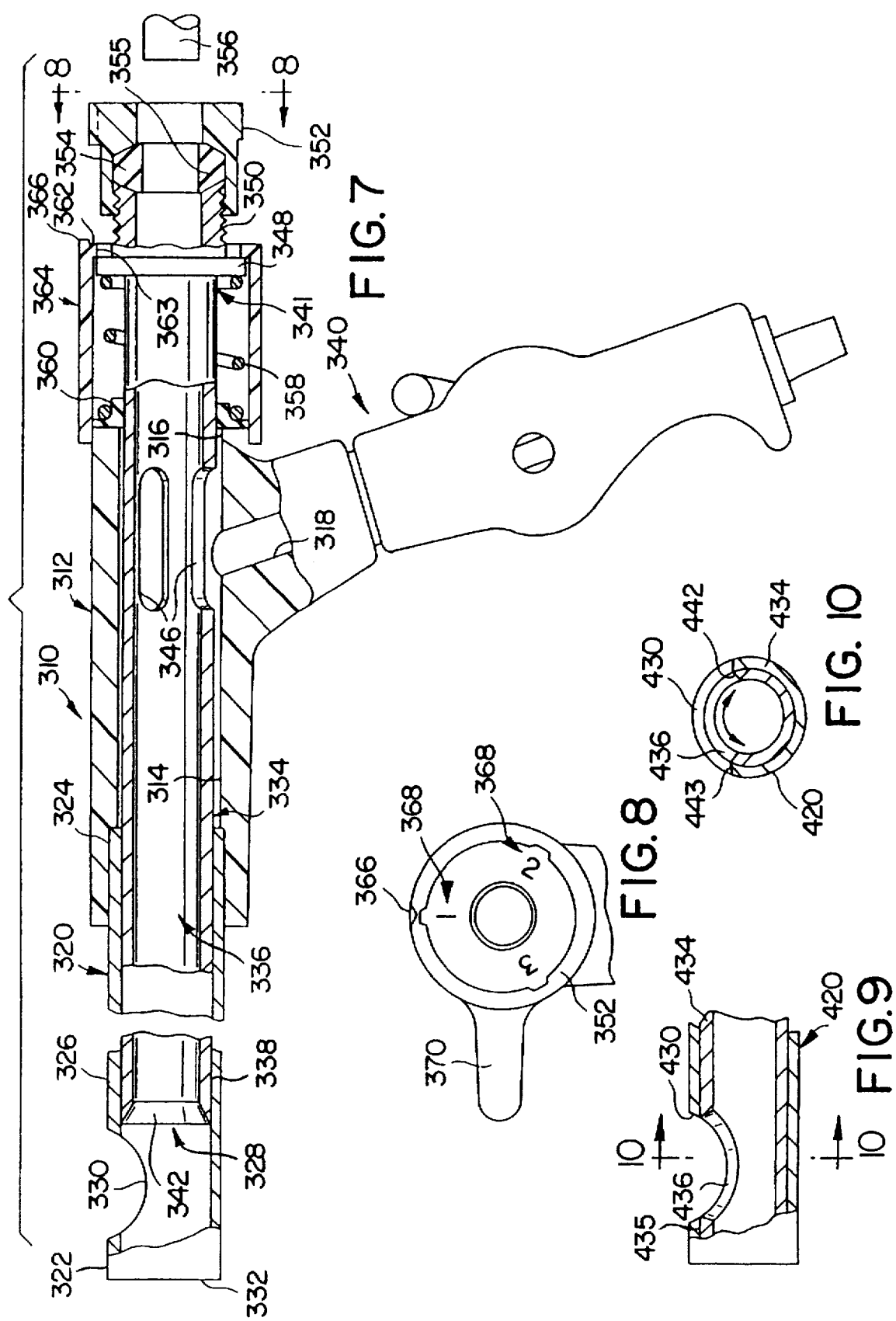

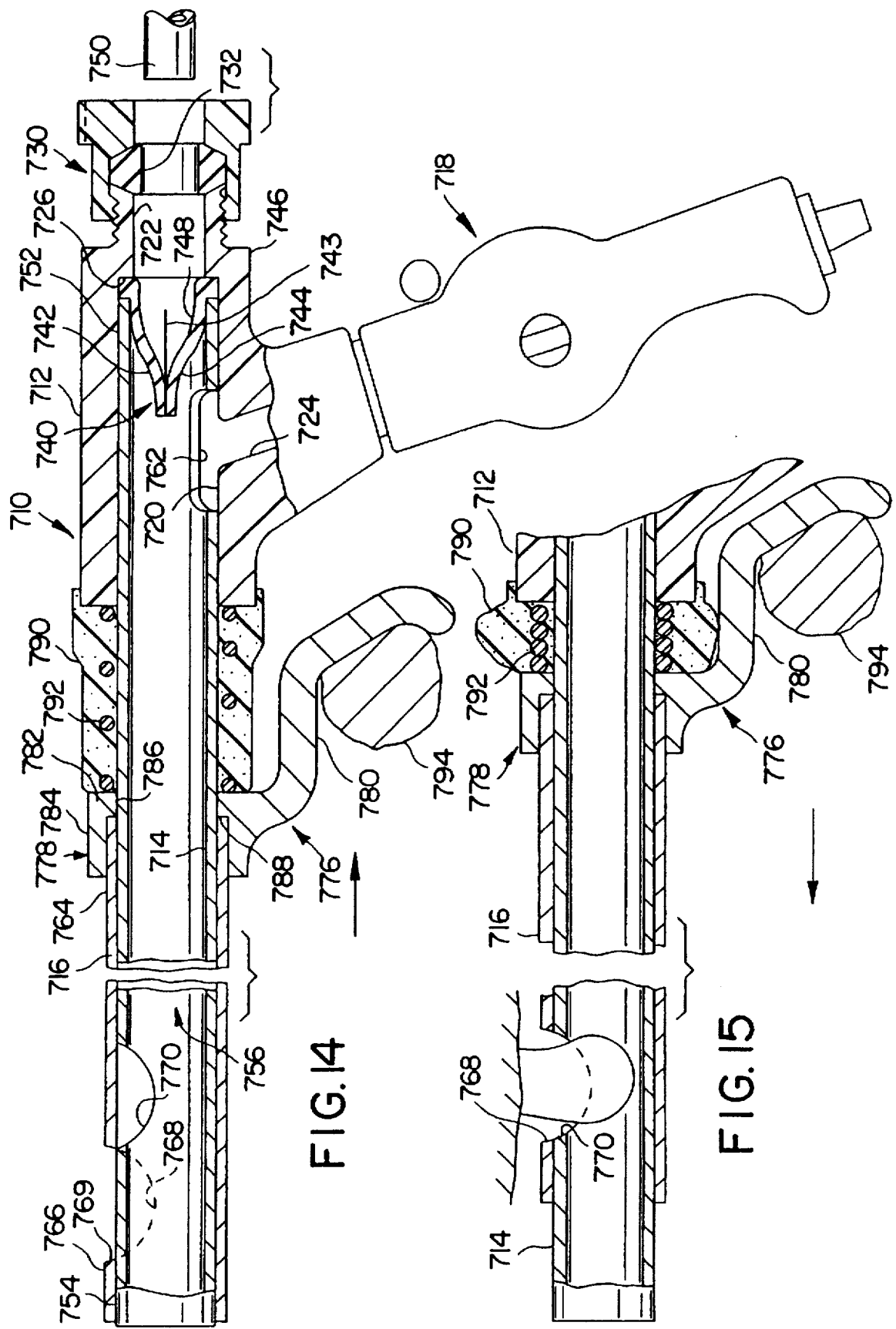

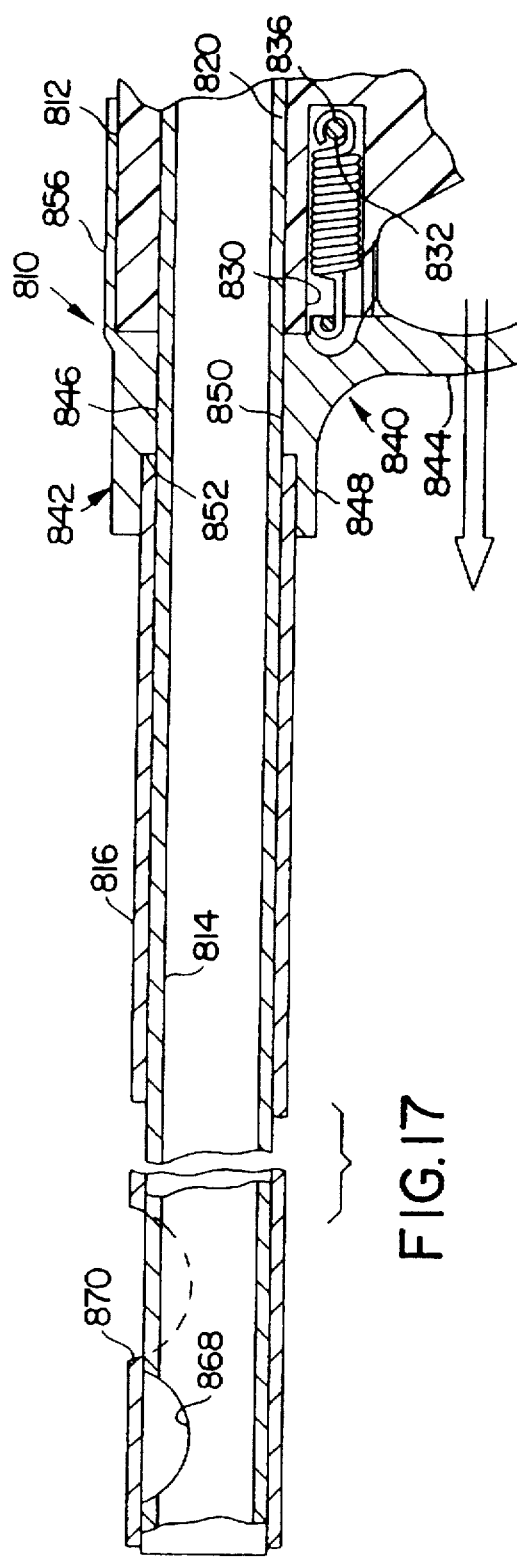
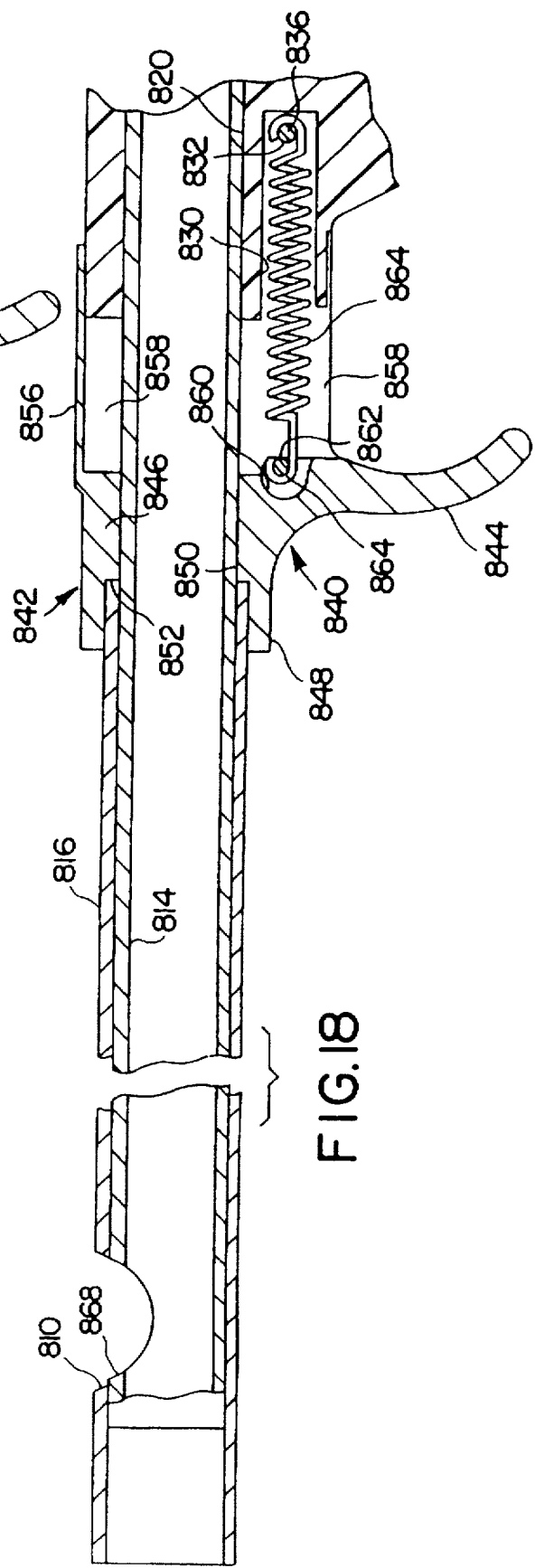

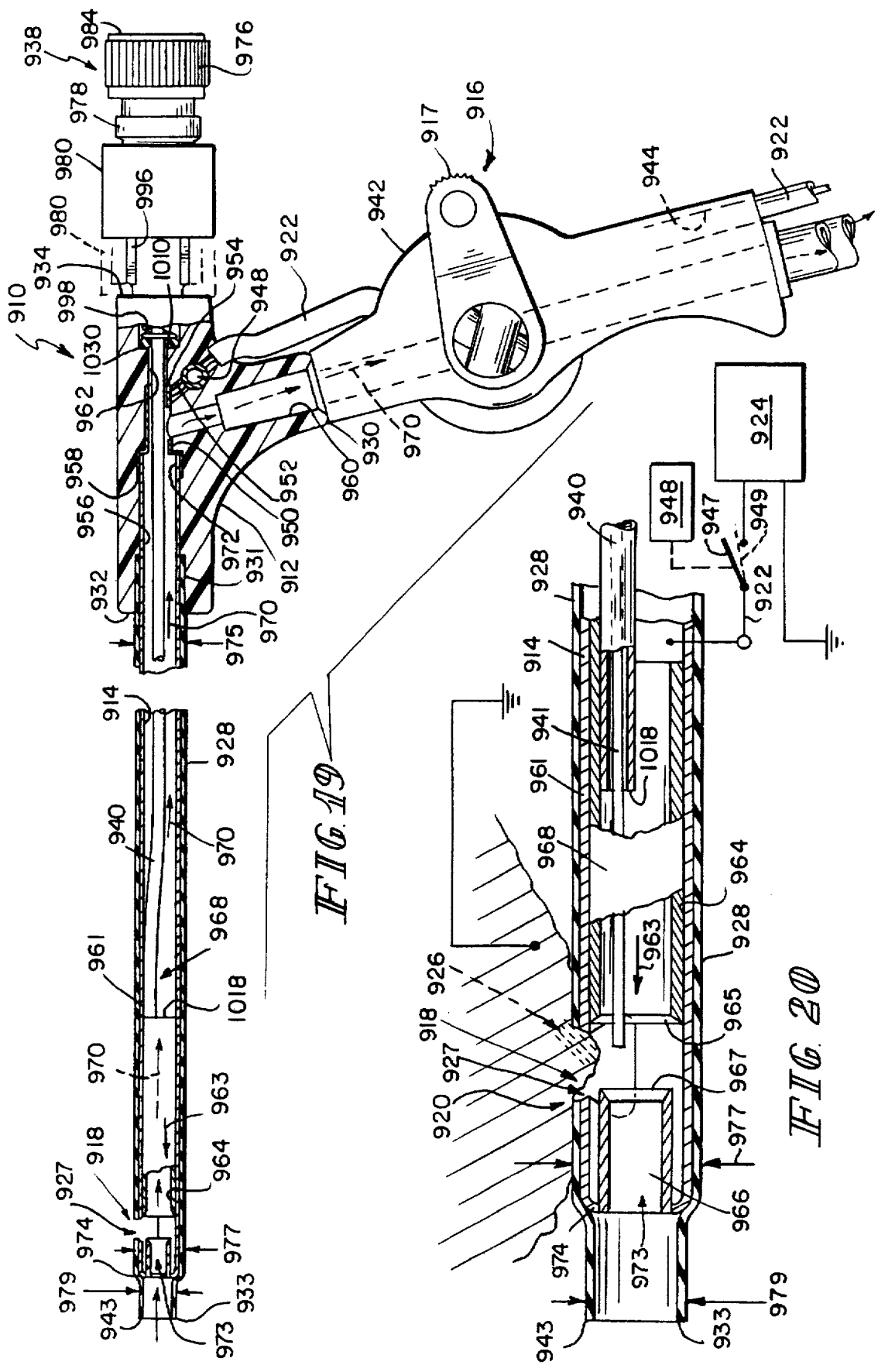

ELECTROCAUTERY CUTTER

This is a continuation in part application of U.S. patent application Ser. No. 08/060,423, to Clement, filed May 11, 1993 and now U.S. Pat. No. 5,505,210 to Clement issued Apr. 9, 1996, which is a continuation in part application of U.S. patent application Ser. No. 07/956,601, filed Oct. 5, 1992 and now U.S. Pat. No. 5,335,671, to Clement, issued Aug. 9, 1994, which is a continuation in part application of U.S. patent application Ser. No. 07/830,580, filed Feb. 4, 1992 and now U.S. Pat. No. 5,409,013 to Clement, issued Apr. 25, 1995, which is a continuation in part application of U.S. patent application Ser. No. 07/580,945, to Clement at al., filed Sep. 11, 1990 and now abandoned, which is a continuation in part application of U.S. patent application Ser. No. 07,432,084, filed Nov. 6, 1989 and now U.S. Pat. No. 5,019,054, to Clement et al., issued May 28, 1991.

The present invention relates to irrigation and suction lavage assemblies and particularly to lavage assemblies configured to allow cutting. More particularly, the present invention relates to an electrocautery cutter lavage assembly that is connected to a source of electrical energy to permit the assembly to cauterize an open wound at a cutting site.

Removal of tissue from a patient's body for disposal or analysis is commonly required in surgical procedures. Typically, cutting instruments have been used to separate small portions of tissue from the patient's body, and grasping or suction devices have been used to retrieve the tissue. For removal of small organs or tissue in laparoscopic or endoscopic surgical procedures, combination instruments that combine cutting and suction functions are known. Such dual function cutting/suction instruments can include a cutting instrument disposed inside a tube having a notch or other opening to permit the cutting instrument to have selective access to body tissue.

It is also known to provide an electrosurgical device for laparoscopic use in tissue dissection and coagulation. See, for example, U.S. Pat. No. 5,273,524 to Fox et al.

What is needed is an improved electrocautery cutter. An improved electrocautery cutter that allows the cutting, suction, and electrocautery functions to be carried out single-handedly by a surgeon would be highly desirable.

The present invention provides an electrocautery cutter with provisions for cutting tissue, removing fluid and the cut body tissue by suction, providing irrigation, and cauterizing the wound during laparoscopy surgery. Preferably, the entire assembly is only used once, and is constructed from low-cost, easily disposable materials.

According to the present invention, the electrocautery cutter includes a rigid cannula defining a cannula interior. The cannula has a proximal end and a distal end that is insertible and positionable in a patient's body. The cannula defines a cannula opening adjacent the distal end to permit access to the cannula interior for capture of body tissue in the cannula interior. The electrocautery cutter further includes a movable cutter for cutting tissue that enters the cannula opening and a cutter actuator configured to move the cutter.

A valve is connected to the cannula to control irrigation and suction flows to the cannula interior. A valve actuator is provided to actuate the valve. An electrical switch is linked to the cannula to control mono-polar electrocautery current flowing from adjacent the distal end of the electrocautery cutter to the patient. An electrical actuator is provided to activate the electrical switch.

The cannula and valve are integrated into a rigid conduit piece structure to be held in one hand. Movement of the rigidly coupled cannula and valve by a user's hand allows the distal end of the cannula to be accurately positioned at a specific location in the patient's body. The cutter actuator, valve actuator, and electrical actuator are operable by a hand of the user as it moves the rigidly coupled valve and cannula to accurately position the distal end of the cannula in the patient's body.

In preferred embodiments of the present invention, a stationary insulation sheath is fixed to the cannula to control the flow of electrocautery current from the cannula to the patient. Cauterizing occurs when a user activates the electrical switch to permit electrocautery current to flow from a non-insulated portion of the cannula that contacts body tissue.

The insulation sheath includes a proximal end situated in the rigid conduit piece structure, a distal end spaced apart from the proximal end and extending past the distal end of the cannula, and an aperture or notch formed adjacent the distal end. The insulation sheath notch is situated adjacent the cannula opening formed in the cannula so that body tissue may enter the cannula interior through the insulation sheath notch and the cannula opening. When a user activates the electrical switch, the electrocautery cutter cauterizes body tissue contacting the cannula at the cannula opening because it is the only non-insulated portion of the cannula touching the patient.

In another preferred embodiment of the present invention, a stationary insulation sheath includes a proximal end situated in the rigid conduit piece structure, a distal end spaced apart from the proximal end, and a notch formed adjacent the distal end of the insulation sheath and situated adjacent the cannula opening formed in the cannula. In this embodiment, the distal end of the cannula extends past the distal end of the stationary insulation sheath so that the distal end of the cannula is exposed and non-insulated. When a user activates the electrical switch of the alternative embodiment, cauterizing also occurs where body tissue contacts the distal end of the cannula and the cannula opening. Cauterizing at the distal end of the cannula is helpful when a "bleeder" is encountered during surgery.

In preferred embodiments of the present invention, the electrocautery cutter further includes a valve configured to control the flow of irrigation fluid, vacuum, and cut body tissue through the cannula. A mechanism is provided on the rigid structure to permit a user to control the flow of irrigation fluid and vacuum with the same hand that controls the cutter and electrical switch.

Additional objects, features, and advantages of the invention will become apparent to those skilled in the art upon consideration of the following description of a preferred embodiment exemplifying the best mode of carrying out the invention as presently perceived.

BRIEF DESCRIPTION OF THE DRAWINGS

FIG. 1 is a cross sectional side view of a tissue removal assembly including a cannula having a notch defined in its distal end, a cutter movably positioned inside the cannula, and a handheld rotary valve (partially shown) extending from the conduit piece to provide a pistol-type grip;

FIG. 2 is a sectional side view of the distal end of the cannula illustrated in FIG. 1, showing the position of tissue caught by oppositely directed catches and maneuvered into the cannula interior through the notch to allow tissue dissection and removal for analysis or disposal of small pieces of tissue;

FIG. 3 is a sectional side view of the distal end of the cannula illustrated in FIGS. 1 and 2, showing the positioning of a fiber optic cable in a tube interior of a tube attached to the cutter, the fiber optic cable acting to convey laser energy for vaporization of tissue positioned in the cannula interior;

FIG. 4 is a sectional view of an alternative embodiment of a distal of the cannula illustrated in FIGS. 1–3, wherein the tip of the cannula is closed to present a laser energy absorbing or dissipating surface to reduce the risk of inadvertent burning or vaporization of tissue;

FIG. 6 is a sectional view of an alternative embodiment of the tissue removal assembly of FIGS. 1–3, wherein the movement of the cutter is controlled by a vacuum powered mechanism attached to the conduit piece and connected to reciprocatingly move the tube and attached cutter;

FIG. 7 is a partial sectional view of an alternative embodiment of a tissue removal assembly wherein a reciprocating cannula has a cutting tip and extends the length of the outer cannula and provides a passageway for other surgical instruments to be positioned adjacent the tissue to be removed;

FIG. 8 is an end view of the embodiment of FIG. 7, as seen from the right, showing numerical indicia and an indexing mark;

FIG. 9 is a partial view of an alternative embodiment of the tip of the apparatus having a notch positioned adjacent the distal end of the inner cannula, wherein the notches in the inner and outer cannulas are configured to be rotated relative to each other to cut tissue;

FIG. 10 is a cross-sectional view taken along lines 10—10 of FIG. 9 showing reversed bevelled edges in the inner and outer cannula notches to provide a scissors-type cutting action;

FIG. 14 is a side view of an alternative embodiment having an outer cannula that is movable relative to an inner cannula, wherein the outer cannula is retracted to align notches formed in the inner and outer cannulas and released to cut tissue trapped in the notches;

FIG. 15 is a view of the tip end of the embodiment of FIG. 14 showing the notches aligned to allow tissue to extend into the interior of the inner cannula in preparation for cutting;

FIG. 17 shows an alternative embodiment having an outer cannula that is movable relative to an inner cannula, wherein the outer cannula is extended to align notches formed in the inner and outer cannulas and is released to cut tissue trapped in the notches;

FIG. 18 shows the embodiment of FIG. 17 with the outer cannula extended and the notches aligned for receiving tissue;

FIG. 19 is a cross sectional side view of a presently preferred embodiment of the present invention showing an electrocautery cutter including a cannula having a cannula opening formed at its distal end, a cutter positioned inside the cannula and configured to be moved by a cutter actuator assembly, a handheld rotary valve, an electrical wire connected to the cannula to provide electrical power to the cannula, and an insulation sheath surrounding the cannula except for the cannula opening formed in the cannula;

FIG. 20 is an enlarged sectional view of a portion of the electrocautery cutter of FIG. 19 showing tissue from a patient's body being situated in the cannula opening formed in the cannula and the insulation sheath extending past the distal end of the cannula so that a surgeon may only cauterize tissue through the cannula opening formed in the cannula;

DETAILED DESCRIPTION OF THE DRAWINGS

Figure 5:
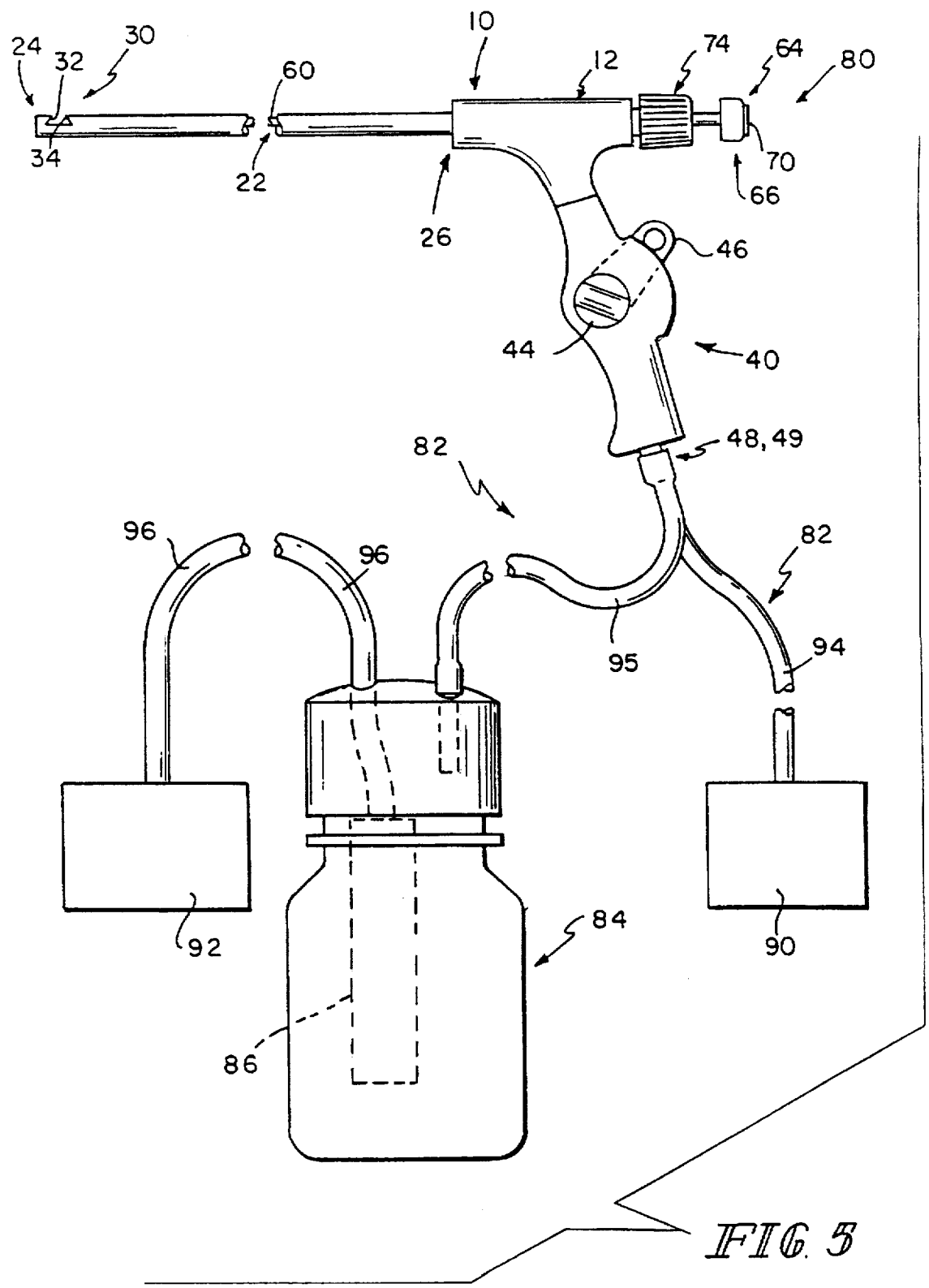
FIG. 5 is a schematic view of a tissue removal system, illustrating the tissue removal assembly of FIG. 1 connected to a tissue sample trap assembly that includes a tissue sample container connected to a vacuum source.

Various embodiments of tissue removal assemblies and electrocautery cutters are shown in FIGS. 1–23. As best illustrated in FIG. 1, a tissue removal assembly 10 useful for laparoscopic, endoscopic, or other surgical procedures includes a conduit piece 12 interconnecting a cannula 20 and a handheld rotary valve 40. Suitable handheld rotary valves are described in U.S. Pat. No. 5,019,054, to Clement et al., issued May 28, 1991, and assigned to Mectra Labs, Inc., the disclosure of which is herein incorporated by reference. Typically, a surgeon supports the assembly 10 with one hand holding the handheld rotary valve 40, leaving the other hand free for manipulation of other instruments.

The tissue removal assembly 10 is useful for removing small organs, scar tissue, growths, biopsy samples, or other tissue from a patient's body. The tissue removal assembly 10 can also be used to destroy tissue at an operative site by laser ablation, or can alternatively be used to cut away tissue for later analysis or disposal.

In preferred embodiments, the tissue removal assembly 10 is disposed of after a single use, minimizing problems related to sterilization, storage, and maintenance of reusable instruments. Construction from low cost, easily incinerated or disposed of materials, which may include molded plastics, is contemplated.

The conduit piece 12 is formed to internally define a first channel 14, a second channel 16, and a third channel 18. All three channels 14, 16, and 18 substantially define respective cylindrical volumes, with first channel 14 having a slightly greater inner diameter than the second channel 16. The third channel 18 has an inner diameter intermediate between that of the first and second channels 14 and 16. The first channel 14 and second channel 16 are connected in fluid communication, and are colinearly defined to allow straight passage therethrough of linearly extending objects. The third channel 18 is also in fluid communication with channels 14 and 16, and connects substantially perpendicular to and between the channels 14 and 16. As will be appreciated with reference to FIG. 1, the interconnections between the channels 14, 16, and 18 can be characterized as a "T-type"

connection. However, provision of "Y"-type connections or other arrangements known in the art for fluid interconnection of channels 14, 16, and 18 is contemplated.

As shown in FIG. 1, the cannula 20 extends longitudinally in a straight line, although curved, bent, flexible, or other conventional cannula designs are also contemplated. The cannula 20 has a distal end 24 for insertion into a patient's body and a proximal end 26 connected to the conduit piece 12. The distal end 24 of the cannula 20 terminates in a tip opening 28 that allows ingress or egress of solids, liquids, or gasses from a cannula interior 22 defined by the cannula 20. The cannula interior 22 is defined between the respective distal and proximal ends 24 and 26 of the cannula 20 to accept and allow bidirectional passage therethrough of solids, liquids, or gasses. Fluids, instruments, or gasses can be introduced from the proximal end 26 for effective operation in a patient's body at the distal end 24, or fluid (blood, etc.), solids (such as tissue samples), or gasses (such as may be produced by laser ablation and vaporization) at the operating site can be withdrawn from the distal end 24 through the cannula interior 22.

The cannula 20 is dimensioned to conformably fit into the first channel 14 of the conduit piece 12, and is rigidly held in position by adhesives, welding, friction tight fit, or other suitable attachment mechanism to the conduit piece 12. Since the proximal end 26 of the cannula 20 is held within the first channel 14, fluid communication (as well as passage of medical instruments or tissue samples) is maintained between the second and third channels 16 and 18, and the cannula interior 22.

The distal end 24 of the cannula 20 is configured to assist in capture and retention of body tissue 36 at an operating site in a patient's body. As is illustrated in FIGS. 1 and 2, a notch 30 is defined in the distal end 24 of the cannula 20, immediately adjacent to the tip opening 28 of the cannula 20. Like the tip opening 28, the notch 30 allows access to the cannula interior 22. The notch 30 is cut in the cannula 20 to define a first catch 32 and an oppositely directed second catch 34. As illustrated in FIG. 1, the notch 30 is formed by removal of a portion of the distal end 24 of the cannula 20. Two cuts into cannula 20 are made along oppositely directed planes indicated by lines b and c (planes b and c both extend perpendicular to the page in the illustration). The cuts along planes b and c terminate at their respective intersection with longitudinally directed planes indicated by lines a and d (planes a and d also extend perpendicular to the page). When a line of intersection between planes b and c is defined outside the cannula 20 (the line extends perpendicular to the page and is represented by a point e), a dihedral angle ba between planes b and c is defined. Typically, the dihedral angle bc is between about 30 degrees and 150 degrees, and is illustrated in FIG. 1 as about 60 degrees.

In practice, the notch 30 and catches 32 and 34 can be easily formed by three cuts into the cannula 20 along planes a, b, and c. More complex cutting, forming, molding, or castings can also be used to provide catches of differing shape. In addition, instead of forming catches from the body of the cannula, it is also contemplated to provide oppositely directed catches attached or affixed to a cannula adjacent to a notch. Multiple catches or several notches may also be used to enhance tissue grabbing or retention effectiveness.

In operation, as illustrated in FIG. 2, catches 32 and 34 enhance tissue grabbing and holding effectiveness, allowing a surgeon to maneuver the distal end 24 to catch and hold a piece of body tissue 36. After body tissue 36 has been positioned in the notch 30, a cutter 50 can be moved forward from its position in the cannula interior 22 toward the distal end 24 of the cannula 20 to cut and/or assist in retaining tissue in the notch 30.

As illustrated in FIG. 1, the cutter 50 has a substantially tubular configuration, defining a cutter passageway 54 therethrough. In addition, the distally directed end of the cutter 50 has a sharpened edge 52. To enhance cutting efficiency, the sharpened edge 52 is created by a traverse, slanting, and non-perpendicular cut across the cutter 50. The resultant elliptically shaped cylinder edge is sharpened to give a beveled edge, with the bevel being directed inward toward the cannula interior 22. Of course, perpendicular cuts across a cutter to give a circular edge, or other cutter edge configurations apparent to those skilled in the art may be substituted for the illustrated cutter embodiment.

The cutter 50 is sized to snugly fit into the cannula interior 22, with its outer diameter being slightly less than the inner diameter of the cannula 20. As illustrated in FIG. 2, when tissue has been engaged by catches 32 and 34 and maneuvered into the cannula interior 22 through the notch 30, the cutter 50 is moved forward from its normal position on the proximal side of the notch 30 in the cannula interior 22, to a cutting position in the region of the notch 30 (position of cutter 50 indicated by dotted outline). When the cutter 50 passes through the cannula interior 22 to cover the region of the notch 30 (adjacent to tip opening 28) any tissue entrapped in the cannula interior 22 is severed by the sharpened edge 52. This severed, dissected tissue can be drawn by surgical instruments, or preferably by suction pressure, through the cutter passageway 54, toward the distal end 24 of the cannula interior 22, into the third channel 18 of the conduit piece 12 and through the handheld rotary valve 40 to a storage or disposal site.

The cutter 50 is moved by a movable assembly 64. The movable assembly 64 includes a button 66 that defines a passageway 68 therethrough. The passageway 68 is breachably sealed by seal 70 in adhesive or welded attachment to the button 66. A tube 60, having a tube interior 62, is attached to extend between the cutter 50 and the button 66. Movement of the button 66 toward the conduit piece 12 consequently causes the cutter 50 to move toward the distal end 24 of the cannula 20.

The cutter 50 is moved back toward the proximal end 26 of the cannula 20 by action of an expansion spring 72. The expansion spring 72 is biasably positioned between the conduit piece 12 and the button 66 to press the button 66 away from the conduit piece 12. When the button 66 is not manually pressed toward the conduit piece 12, this outward (away from the conduit 12) biased force is resisted by a block 74 attached to the conduit piece 12 and configured to partially surround button 66. The spring arrangement is configured to promote manually operated reciprocating motion, with the rest, or normal, position of the cutter 50 (attached by way of tube 60 to the button 66) selected to be on the proximal side of the notch 30, leaving the notch 30 normally open to accept body tissue. Of course, as those skilled in the art will appreciate, it is alternatively contemplated to reverse the biased spring direction, so that a cutter 50 is normally positioned on the distal side of the notch, with the cutter having its proximal edge sharpened.

In addition to separation of tissue from a patient's body by cutting action of the cutter 50, tissue can optionally be removed by application of laser energy to ablate and vaporize tissue. As illustrated in FIG. 1 and FIG. 3, delivery of laser energy (indicated by arrows 39 in FIG. 3) to tissue 36 is enabled by passage of fiber optic cable 38 inserted, respectively, through breachable seal 70, passageway 68 of button 66 (seal 70 and button 66 illustrated in FIG. 1), and tube interior 62 of tube 60. In operation, the tissue 36 is maneuvered into position through the notch 30, and laser energy is transmitted through the fiber optic cable 38 from a laser light source (not shown) to vaporize the tissue 36.

An alternative cannula tip embodiment suitable for dual mechanical cutter/laser removal of tissue is illustrated in FIG. 4. A cannula 220 (substantially similar to cannula 20) having a notch 230 therein is used to entrap tissue 236. The distal end of the cannula 220 is closed with a tip wall 200. The tip wall 200 can be coated or otherwise prepared to have a laser absorptive or dissipative surface that reduces back reflection of laser energy transferred through fiber optic cable 238 (positioned in tube interior 262 of tube 260) to the tissue 236. In operation, after the tissue 236 is firmly positioned in the notch 230, the cutter 250 can be moved forward to substantially cover the notch 230. This reduces escape of fumes or burned tissue into the patient's body. Of course, the cutter 250 can still alternatively be used without recourse to laser energy to dissect and remove tissue.

Dissected tissue or fumes from vaporized tissue are removed from the cannula by suction (indicated by arrow 37 in FIGS. 2-3, and arrow 237 in FIG. 4) produced by fluid connection to one of vacuum sources 90 and 92 illustrated in FIG. 5. As illustrated in FIG. 5, a tissue removal system 80 includes a tissue storage apparatus 82 connected to tissue removal assembly 10 such as previously described. The tissue storage apparatus 82 includes a sample container 84, conduits 94, 95, 96, and vacuum sources 90 and 92. Conduit 94 is connected in fluid communication between inlet 49 of the rotary valve 40 and vacuum source 90. Conduit 95 is connected in fluid communication between inlet 48 of the dual inlet port rotary valve 40 and vacuum source 92. Conduit 96 is connected to a screen 86 positioned inside sample container 84, allowing fluid communication between the sample container 84 and vacuum source 92 but limiting passage of solid tissue samples.

In operation, disposal of tissue samples entrained in the cannula interior 22 of the cannula 20 involves turning the handle 46 of the rotary valve 40 to bring the rotor 44 into a position that allows fluid communication between vacuum source 90 and cannula interior 22. Solid, liquid, or gas waste that is present in the cannula interior 22 are drawn by suction toward the proximal end 26 of the cannula 20, and through the third channel 18 into the rotary valve 40. The wastes continue through the conduit 94 and into the vacuum source 90 for disposal.

If samples of tissue are desired for analysis, the handle 46 of the rotary valve 40 is turned to bring the rotor 44 into a position that allows fluid communication between vacuum source 92 and cannula interior 22. A solid tissue sample dissected from a patient's body and present in the cannula interior 22 are drawn by suction toward the proximal end 26 of the cannula 20, and through the third channel 18 into the rotary valve 40. The sample is drawn by suction through the conduit 95 and into the sample container 84 for storage. Continued passage of the sample (not shown) through the conduit 96 and into vacuum source 92 is prevented by a screen 86 that allows fluid flow but prevents passage of tissue sample sized solids.

An alternative embodiment of the invention in which movement of a cutter is controlled by application and release of a vacuum is illustrated in FIG. 6. A tissue removal assembly 110 includes a cannula 120 connected to a conduit piece 112 and a valve 140. The conduit piece 112 is formed to define first, second and third channels 114, 116, and 118, with the cannula 120 being inserted into the conduit piece 112 to fit into first channel 114. In addition, like the embodiment of the invention illustrated in FIG. 1, a cutter 150 can be moved through the cannula 120 to alternately block notch 130 or allow passage through the notch 130 of body tissue (not shown).

The cutter 150 is attached to a tube 160 configured to support a fiber optic cable capable of transferring laser energy to an operative site. Although use of a laser is not always required, its ready availability allows a surgeon to select to use the laser alone, the cutter alone, or both the laser and the cutter as necessary to optimize surgical treatment.

The tube 160 passes through the cannula 120 and into conduit piece 112, where it passes in substantially gas tight sliding seal through neck 195 of the second channel 116. The sliding seal in neck 195 can optionally be enhanced by the use of lubricants or low frictional resistance polymeric coatings. Of course, as those skilled in the art will appreciate, breachable elastomeric seals, annular seals, or other conventional sliding seals can be used.

After passing through neck 195, the tube 160 enters chamber 182 of a vacuum powered mechanism 180. The vacuum powered mechanism 180 is a low cost, disposable mechanism attached to the conduit piece 112 to allow a surgeon to control movement of the cutter 150. The chamber 182 of the mechanism 180 is configured to define an air inlet 188, a passageway 189, and a vacuum port 194 for connection by way of valve 192 to a vacuum source 196. Valves such as described in U.S. Pat. No. 5,019,054, to Clement et al., issued May 28, 1991, are preferred, although of course other conventional valves or mechanisms for controlling application of vacuum and allowing admission of air into chamber 182 are also suitable. In other contemplated embodiments, a separate valve positioned between the chamber 182 and the vacuum source is not required. As those skilled in the art will appreciate, the vacuum source 196 can be directly controlled to provide pulsatile, oscillatory, or other predetermined suction action to withdraw air from the chamber 182.

The air inlet 188 defined by chamber 182 is normally open to atmosphere, and passageway 189 is sealed by a breachable seal 190 adhesively attached to the chamber 182. The chamber 182 is dimensioned to allow placement of helical spring 186 or other suitable energy storing resilient piece (eg. leaf springs) into the chamber 182. The spring 186 is positioned between a sliding piston 184 and the conduit piece 112. As will be appreciated by those skilled in the art, the position of a spring or resilient piece in the chamber 182 can be varied to accommodate differing spring directions (i.e. biased to resist motion either away or toward the conduit piece 12). In addition, by providing suitable interconnections between the piston 184 and a spring, it is contemplated to mount the spring outside the chamber, rather than inside as illustrated.

The sliding piston 184 is positioned in sliding, gas tight movement in chamber 182. The piston 184 is attached to tube 160, and is configured to have a passageway therethrough (not shown) in fluid communication with the tube 160. Presence of the passageway through the piston 184 allows a surgeon to insert a fiber optic cable (not shown) through the seal 190 and passageway 189, and continue insertion through the passageway of piston 184 into tube 160 for positioning at the surgical site.

Operation of the assembly 110 is similar to operation of assembly 10 illustrated in FIG. 1, with the following difference in cutter actuation. Instead of manually pressing button 66 of assembly 10 to move the cutter 50, use of assembly 110 requires operating valve 192 to open a fluid connection between chamber 182 and vacuum source 196. Air present in chamber 182 rushes out through port 194, causing movement of the piston 184 (or other devices that move in response to pressure changes such as a diaphragm) toward the conduit piece 112. Movement of the piston 184 simultaneously compresses the spring 186 to store energy, and moves the cutter 150 (attached to the piston 184 by tube 160) forward through the notch 130 of the cannula 120, cutting any tissue contained therein. After the cutter has moved forward, the valve 192 can be moved to a position allowing influx of air at normal atmospheric pressure into the chamber 182, which in turn allows release of spring 186 and movement of the piston 184 and attached tube 160/cutter 150 away from the notch 130. The valve 192 can be moved to an open position to repeat the foregoing operation.

In the alternative embodiment of FIG. 7, the tissue removal assembly 310 includes a conduit piece 312 having first, second, and third channels 314, 316, and 318, respectively, with the third channel 318 attached to a vacuum source (not shown) through a handheld rotary valve 340. A suitable handheld rotary valve is described in U.S. Pat. No. 5,019,054 to Clement et al. The handheld rotary valve 340 is rigidly attached to the conduit piece 312 to form a pistol grip. Thus, by grasping the rotary valve 340, the surgeon has positive control of the placement and positioning of the distal end 322 of the cannula 320.

The first and second channels 314, 316 are coaxially aligned, and the third channel 318 joins the first and second channels 314, 316 at an angle to the axis. An outer cannula 320 has an open distal end 322, an open proximal end 324, and a side wall 326 defining a first interior region 328 that extends between the distal and proximal ends 322, 324, respectively. Proximal end 324 of the cannula 320 is dimensioned to conformably fit into the first channel 314 of the conduit piece 312, and is rigidly held in position by adhesives, welding, friction-tight fit, or other suitable attachment mechanism to the conduit piece 312. Since the proximal end 324 of the cannula 320 is held within the first channel 314, fluid communication is maintained between the second and third channels 316, 318, respectively, and the interior region 328. Moreover, the coaxial alignment of the first and second channels 314, 316, which illustratively are of the same general diameter, allows passage of medical instruments through the conduit piece to the open distal tip end 322 of the cannula 320.

The distal end 322 of the cannula 320 is configured to assist in capture and retention of body tissue at an operating site in a patient's body. A notch 330 is defined in the distal end 322 immediately adjacent the tip opening 332 of the cannula 320 and allows tissue to enter the interior region 328. The tip opening 332 allows medical instruments, such as a cauterizing device, that have been passed through the first and second channels 314, 316 and the outer cannula 320 to be positioned at the operating site.

An inner cannula 334 has an open distal end 338 and an open proximal end 341, and a second interior region 336 therebetween. The distal end 338 of the inner cannula 334 has a sharpened bevelled edge 342, with the bevel being directed inwardly toward the second interior region 336 as shown in FIG. 7.

The inner cannula 334 is sized to snugly fit into the first interior region 328. A plurality of longitudinal slots 346 are formed circumferentially around the inner cannula 334. The slots 346 are axially co-located with the junction between the first and second channels 314, 316, and the third channel 318. The slots 346 are sized and positioned to ensure that at least a portion of the third channel 318 of the conduit piece 320 is always in fluid communication with the second interior region 336 of the inner cannula 334. In order to avoid vacuum leaks between the inner cannula 334 and the second channel 316, an annular grommet 360 is configured to abut the proximal end of the second channel 316 and fit around the outside of the inner cannula 334. The inner cannula 334 also includes a spring-retaining flange 348 that extends radially outwardly from the proximal end 341 of the inner cannula 334.

An externally threaded annular projection 350 extends axially from the spring-retaining flange 348 in the direction away from the distal end 338 of the inner cannula 334. An internally threaded compression member 352 engages the externally threaded annular projection 350. A compressible cannula seal 354 having a central aperture 355 is disposed between the compression member 352 and the annular projection 350. Threading the compression member 352 onto the annular projection 350 squeezes the compressible seal 354 therebetween to close the central aperture 355.

When the compression member 352 is fully engaged with the annular projection 350, central aperture 355 is completely closed to restrict the entry of air or other contaminants into the second interior region 336. As the compression member 352 is unscrewed from the annular projection 350, the central aperture 355 opens to allow insertion of a medical instrument 356 into the second interior region 336 of the inner cannula 334.

A conduit piece extension member 364 is rigidly attached to the conduit piece 312 by welding, threading, or the like. A perimetral shoulder 362 is formed on the extension member 364 to extend inwardly toward the longitudinal axis of the inner cannula 334. The perimetral shoulder 362 defines an aperture 363 that is sized to permit axial movement of the annular projection 350 and the compression member 352 while blocking passage of the spring retaining flange 348 therethrough.

A return spring 358 is positioned between the annular grommet 360 and the spring-retaining flange 348. The return spring 358 urges the spring-retaining flange 348 into contact with the perimetral shoulder 362, which interferes with the axial movement of the spring-retaining flange 348. At the same time, the return spring 358 retains the annular grommet 360 in sealing engagement with the proximal end of the conduit piece 312. The perimetral shoulder 362 is axially positioned so as to maintain the sharpened edge 342 of the inner cannula 334 in a normal, or rest, position that is proximal to the notch 330 when the flange 348 is positioned against the shoulder 362.

Using a circular cross section for the outer cannula 320 and inner cannula 334 advantageously allows multiple cutting segments using the same inner cannula 334 by simply rotating the inner cannula 334 inside the outer cannula 320. When a first portion of the sharpened edge 342 becomes dulled by use, rotation of the inner cannula 334 presents a different portion of the sharpened edge 342 to tissue entrapped in the notch 330. Depending upon the size of the notch 330, a single inner cannula 334 can effectively have 2, 3, or more cutting portions of the sharpened edge 342.

As illustrated in FIG. 8, an indexing mark 366 can be formed on the proximal end of the conduit piece extension member 364. A numerical indicia 368 can be incorporated into the compression member 352, as illustrated in FIG. 9, to cooperate with the indexing mark 366. As the inner cannula 334 is rotated to present a different portion of the sharpened edge 342, the numerical indicia 368 provides a positive indication to the surgeon of the remaining unused portions of the sharpened edge 342.

In operation, the distal end 322 of the outer cannula 320 is inserted into the patient's body and maneuvered to position tissue to be excised through the notch 330 into the interior region 328. When the tissue is positioned inside the interior region 328, the surgeon pushes on the compression member 352 with his thumb, pushing the inner cannula 334 toward the distal end 322. Alternatively, a thumb engaging outrigger 370, illustratively shown in FIG. 8, can be attached to the compression member 352 to facilitate thumb actuated movement of the inner cannula 334. When the inner cannula 334 covers the region of the notch 330, any tissue trapped in the interior region 328 is severed by the sharpened edge 342. This severed, dissected tissue can be drawn by surgical instruments, or preferably by suction pressure, through the inner cannula 334 through the longitudinal slots 346, through the third channel 318, and finally through the valve 340 to a storage or disposal site. Once the entrapped tissue has been severed and removed, the surgeon can release the thumb pressure on the compression member 352, allowing the return spring 358 to urge the inner cannula 334 to return to its rest position.

In the event that the wound from the severed tissue turns into a bleeder, a cauterizing device can be inserted into the inner cannula to cauterize the wound, if required. The compression member 352 is unthreaded from the annular projection 350 to open the central aperture 355 of the compressible annular seal 354. The cauterizing device is inserted through the compressible seal 354 toward the distal end 322 of the outer cannula. When the cauterizing device is positioned, the compression member 352 is screwed onto the annular projection 350 to close the central aperture 355, providing an airtight seal around the cauterizing device.

It will be appreciated that the cauterizing device could be inserted into the inner cannula 334 prior to commencement of the operation. Moreover, the tissue removal assembly 310 could be a pre-packaged assembly including the cauterizing device. However, to enhance the versatility of the assembly, it would be better to insert the cauterizing device when needed. That option leaves open the possibility of inserting other instruments such as graspers, laser vaporizers, or the like as necessary during the procedure.

An alternative embodiment, as illustrated in FIGS. 9 and 10, shows an inner cannula 434 having an open distal end 435. The inner cannula 434 is formed to include a notch 436 having a bevelled edge, with the notch 436 axially co-located with the notch 430 formed in the outer cannula 420. The edge of the notch 436 is bevelled inwardly as shown in FIG. 10 so as to form a sharpened edge 442 while the edge of the notch 430 is bevelled outwardly to form sharpened edge 443. In this embodiment, the inner cannula 434 is rotated rather than reciprocated inside the outer cannula 420. As the sharpened edge 442 of the notch 436 passes through the notch area 430, any tissue entrapped in the interior region is severed by the scissors-type movement between sharpened edges 442 and 443.

Figure 11:
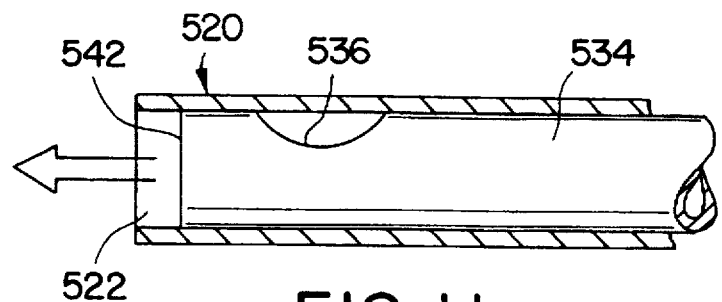
FIGS. 11–13 are three fragmentary views showing the cutting notch in the wall of the inner cannula with the inner cannula extendible out the open end of the outer cannula to be retracted inwardly during the cutting mode to use a scissors-type cutting action between the bevelled edge of the inner cannula notch and the distal end of the outer cannula.
Figure 12:
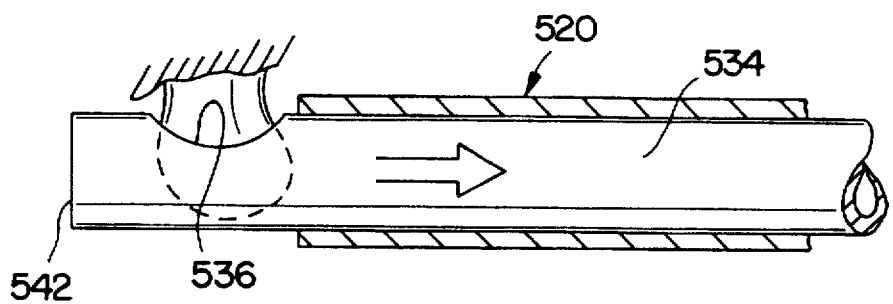
Figure 13:
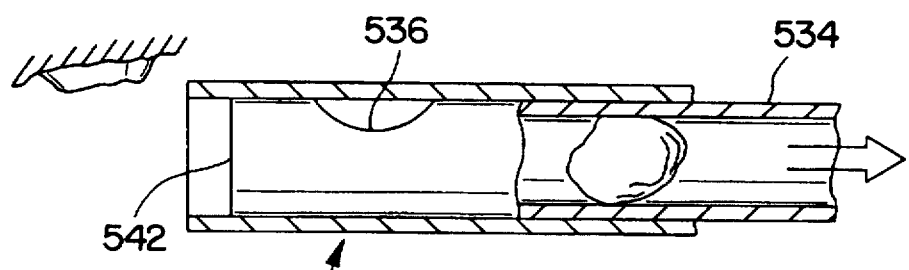

FIGS. 11–13 illustratively shows still another embodiment where the outer cannula 520 has an open end 522. The inner cannula 534 includes a distal end 542 and a notch 536 formed adjacent the distal end 542. The distal end 542 of the inner cannula 534 is preferably open so that instruments may be inserted through the inner cannula 534 and out through the open end 522.

FIG. 11 shows the inner cannula 534 in a normal rest position with the notch 536 positioned inside the outer cannula 520. When the inner cannula 534 is extended distally to expose the notch 536, tissue can be maneuvered into the notch 536, as shown in FIG. 12. As the inner cannula 534 is retracted, tissue trapped in the notch 536 is cut by the scissors-type action between the notch 536 and the distal end 522 of the outer cannula 520. Once severed, the tissue is drawn through the inner cannula 534, as shown FIG. 13, for analysis or disposal.

An irrigation and suction lavage assembly for removal of irrigation fluid and body tissue during laparoscopy surgery can be seen generally with reference to FIGS. 14–18. The lavage assembly includes a conduit piece, inner and outer concentric cannulas coupled to the conduit piece, and means for moving the outer cannula relative to the inner cannula for cutting tissue. Breachable seals for sealing the inner cannula and the conduit piece are coupled to the inner cannula and the conduit piece, respectively. Valve means for controlling the flow of irrigation fluid and cut body tissue through the inner cannula and conduit piece is coupled to the conduit piece.

Figure 16:
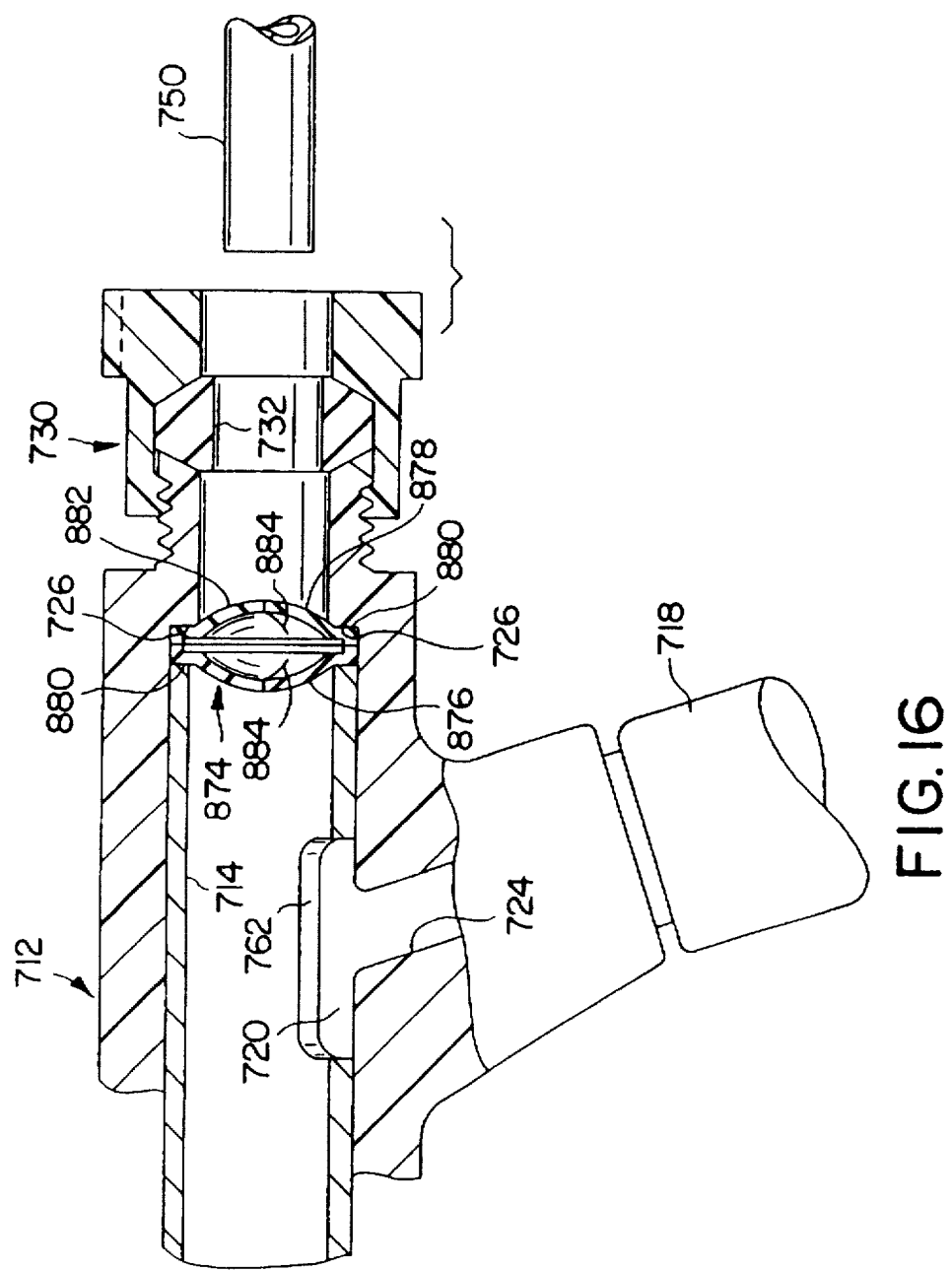
FIG. 16 shows a double duckbill flap valve as an alternative sealing means for breachably sealing the inner cannula.

As shown in FIGS. 14–16, the lavage assembly 710 includes a conduit piece 712, an inner cannula 714, and an outer cannula 716. The conduit piece 712 includes first, second, and third channels 720, 722, and 724, respectively. The first and second channels 720, 722 are coaxially aligned, with the distal end of the second channel 722 opening into the proximal end of the first channel 720. Illustratively, the second channel 722 has a smaller diameter than the first channel 720, thereby defining a shoulder 726 in the conduit piece 712 at the juncture between the first and second channels 720, 722. The third channel 724 intersects the first channel 720 and is in fluid communication with a valve 718.

A valve 718 is coupled to the assembly 710 to control the flow of fluids, gasses, and solids through the assembly 710. A preferred valve is described in U.S. Pat. No. 5,019,054 to Clement et al., and assigned to Mectra Labs, Inc., the disclosure of which is incorporated herein by reference.

The first and second channels 720, 722 are sealed by a duckbill flap valve 740 and a sealing mechanism 730, respectively. A preferred sealing mechanism 730 includes a compressible annular seal 732 and actuating mechanism as described in U.S. Pat. No. 5,456,636 to Clement and assigned to Mectra Labs, Inc., the disclosure of which is incorporated herein by reference.

The duckbill flap valve 740 is positioned in the first channel 720 and is situated in abutting relation to the shoulder 726. The duckbill flap valve 740 is integrally formed to have a first flap 742 biasingly directed in sealing engagement with a second flap 744. Both flaps 742 and 744 are integrally joined to an annular rim 746 having a central aperture 748 through which a medical device 750 can pass. The rim 746 projects radially outwardly from the flaps 742, 744 a distance equal to the thickness of the inner cannula 714 and is conformably fitted against the shoulder 726 and the wall of the first channel 720. The flaps 742 and 744 are separated by a slit 743 that allows the flaps 742 and 744 to separate, moving apart as the medical device 750 is inserted therethrough. The compressible annular seal 732 and the flaps 742 and 744 can be coated with friction reducing compounds to ease insertion or withdrawal of the medical device 750.

The inner cannula 714 has a proximal end 752, a distal end 754, and an interior region 756 extending therebetween. The proximal end 752 of the inner cannula 714 is coupled to the first channel 720 of the conduit piece 712. The outer diameter of the inner cannula 714 is substantially equal to the diameter of the first channel 720, allowing the inner cannula 714 to be inserted into the first channel 720. The inner cannula 714 is inserted until the proximal end 752 of the inner cannula 714 abuts the annular rim 746 formed on the duckbill flap valve 740, thereby holding the duckbill flap valve 740 in position against the shoulder 726. An elongated aperture 762 is formed in the inner cannula 714 and positioned to allow movement of gases, liquids and solids between the interior region 756 and the third channel 724. Any suitable fastening means can be used to attach the inner cannula 714 to the conduit piece 712, such as, welding, gluing or press-tight fit.

The outer cannula 716 is concentrically positioned to surround the inner cannula 714. The inner diameter of the outer cannula 716 is substantially equal to the outer diameter of the inner cannula 714 so as to provide a close, sliding engagement between the inner and outer cannulas 714, 716. The outer cannula 716 includes proximal and distal ends 764, 766, respectively. A first notch 768 is formed adjacent the distal end 766. The edge of the first notch 768 is bevelled outwardly from the outer cannula 716 so as to form a first cutting surface 769.

A second notch 770 is formed adjacent the distal end 754 of the inner cannula 714. The notches 768, 770 are normally positioned in a non-aligned relation to each other, so that access to the interior region 756 of the inner cannula 714 through the notches 768, 770 is barred.

The proximal end 764 of the outer cannula is coupled to a trigger means 776. The trigger means 776 includes a cup portion 778 for engaging the outer cannula 716 and an trigger portion 780 for engaging a digit 794 of a hand operating the removal assembly 710.

The annular cup portion 778 includes a circular base member 782 and a cylindrical side wall 784. The inner diameter of the cylindrical sidewall 784 is substantially equal to the outer diameter of the outer cannula 716. The circular base member 782 includes a central aperture 786 having a diameter substantially equal to the outer diameter of the inner cannula 714. Thus, the circular base member 782 and the cylindrical side wall 784 cooperate to form a shoulder 788. The outer cannula 716 is inserted into the trigger means 776 until the proximal end 764 of the outer cannula 716 abuts the shoulder 788. The now-joined outer cannula 716 and trigger means 776 can slidably engage the inner cannula 714 as a unit. The trigger 780 provides a means for engaging the digit 794 of the surgeon's hand.

A cylinder 790 of elastomeric material surrounds the inner cannula 714, but is not attached thereto. The cylinder 790 is attached to the trigger means 776 and the conduit piece 712, thereby coupling the trigger means/outer cannula 776, 716 to the conduit piece 712. A compression spring 792 is embedded in the cylinder 790 of elastomeric material.

In operation, distal ends 754, 766 of the inner and outer cannulas 714, 716, respectively, of the irrigation and suction lavage assembly 710 are inserted into a patient's body by conventional means. When the lavage assembly 710 is properly positioned at the operating site, the surgeon rotates the valve 718 in a first direction to permit saline solution or other irrigation fluid to flow to the site. When the site is sufficiently clear, the surgeon can turns off the irrigation fluid and pull the trigger 780. Pulling the trigger 780 moves the trigger means/outer cannula 776/716 away from the normal, or rest, configuration in the direction of arrow 795 (FIG. 14). As the outer cannula 716 slides along the inner cannula 714, the notches 768, 770 align to permit tissue 771 to enter the interior region 756, as shown in FIG. 15.

When the trigger means 776 is pulled in the direction of arrow 795, the cylinder 790 of elastomeric material and the spring 792 are compressed between the trigger means 776 and the distal end of the conduit piece 712, storing mechanical energy. When the notches 768, 770 have been aligned, tissue 771 can be maneuvered into the interior region 756 through the aligned notches 768, 770. Once the tissue 771 has been maneuvered into the notches 768, 770, the trigger means 776 is disengaged, thereby releasing the stored mechanical energy to restore the cylinder 790 of elastomeric material and the spring 792 to their original states and move the outer cannula 716 in the direction of arrow 797 (FIG. 15) to its normal, or rest, position.

As the outer cannula 716 moves, the cutting surfaces of the notches 768, 770 move relative to each other, thereby cutting the tissue 771 trapped in the interior region 756. The surgeon rotates the valve 718 in a second direction to connect a vacuum source (not shown) to the inner cannula 714 through the first and third channels 720, 724, respectively. The vacuum draws the cut tissue through the interior region 756, the elongated aperture 762 in the inner cannula 714, and the third channel 724. Once removed, the cut tissue can be stored for later analysis or disposal.

When the tissue 771 is cut, the resulting wound could be a bleeder. In that case, it would be advantageous to be able to present an electrocautery device to the site of the wound. An electrocautery device, or other medical instrument 750, can be inserted through the compressible annular seal 732 and the duckbill flap valve 740 to be presented at the distal end 754 of the inner cannula 714. The distal end 754 can be maneuvered to position the electrocautery device at the tissue removal site to cauterize the injury. Advantageously, the sealing mechanism 730 and the duckbill flap valve 740 cooperate to prevent ingassing or outgassing of fluids through the second channel 722 during the procedure.

The embodiment of FIGS. 17–18 provides for reversing the cutting action of the outer cannula. When the lavage assembly 810 is in the normal or rest position as illustrated in FIG. 17, the notch 870 in the outer cannula 816 is positioned proximal to the notch 868 in the inner cannula 814 in contradistinction to the arrangement of FIG. 14. Thus, the outer cannula 816 is moved axially away from the conduit piece 812 relative to the inner cannula 814 in order to align the notches 868, 870.

The conduit piece 812 is substantially similar to the conduit piece 712 in FIGS. 14–16, but includes first and second holes 830, 832 bored into the conduit piece 812. The first hole 830 is bored into the distal end of the conduit piece 812 to lie parallel to the axis of the first channel 820 of the conduit piece 812. The second hole 832 is bored transversely through the conduit piece 812 to perpendicularly intersect the first hole 830 and receive a first spring retaining dowel 836.

The inner and outer cannulas 814, 816, respectively, are substantially similar to the cannulas in FIGS. 14–16. The trigger means 840 includes an annular cup portion 842 and an outrigger portion 844. The annular cup portion 842 includes a circular base member 846 and a cylindrical side wall 848. The inner diameter of the sidewall 848 is substantially equal to the outer diameter of the outer cannula 816 so as to provide a tight fit. The circular base member 846 includes a central aperture 850 having a diameter substantially equal to the outer diameter of the inner cannula 814. Thus, the circular base member 846 and the cylindrical side wall 848 cooperate to form a shoulder 852 in the cup portion 842. The proximal end of the outer cannula 816 snugly fits inside the cylindrical side wall 848 and abuts the shoulder 852 in the cup portion 842. The outer cannula 816 is rigidly attached to the trigger means 840 by welding, gluing, or other suitable attaching means. The now-joined outer cannula 816 and trigger means 840 slidingly engage the inner cannula 814.

The trigger means 840 in the embodiment of FIGS. 17-18 also includes a skirt portion 856 extending proximally from the circular base member 846. The skirt portion 856 is configured to conform to the general shape of, and extend beyond, the distal end of the conduit piece 812 to partially surround the conduit piece 812. The skirt portion 856 is configured to allow the trigger means 840 and outer cannula 816 to slide along the inner cannula 814 while enclosing the space 858 (FIG. 18) between the circular base portion 846 and the distal end of the conduit piece 812.

A third hole 860 is bored into the trigger means 840 at the juncture between the cup portion 842 and the trigger portion 844 so as to be coaxially aligned with the first hole 830 in the conduit piece 812. The diameter of the third hole 860 is substantially equal to the diameter of the first hole 830. A fourth hole 862 is bored transversely into the trigger means 840 so as to perpendicularly intersect the third hole 860. The fourth hole 862 receives a second spring retaining dowel 864.

An expansion spring 866 extends between the first and third holes 830, 860, respectively, and is retained in position by the first and second spring retaining dowels 836, 864, respectively. Thus, the expansion spring 866 resiliently couples the outer cannula 816 to the conduit piece 812.

The inner and outer cannulas 814, 816 each include a notch 870, 868, respectively, formed in the distal ends thereof. In the embodiment of FIGS. 17-18, however, the relative positions of the notches 868, 870 are reversed as compared to the embodiment of FIGS. 14-15. That is, in FIGS. 17-18, the notch 868 in the inner cannula 814 is distal to the notch 870 in the outer cannula 816. Thus, the embodiment of FIGS. 17-18 operates essentially oppositely to the embodiment of FIGS. 14-15.

In operating the embodiment of FIGS. 17-18, the operator engages the outrigger portion 844 so as to slide the outer cannula 816 from its normal, or rest, position in the direction of arrow 872 (FIG. 17) in order to align the notches 868, 870. The spring 866 is extended to store mechanical energy. When the notches 868, 870 are aligned, tissue is maneuvered into the interior region of the inner cannula 814. When the tissue has been maneuvered through the notches 868, 870, the outrigger portion 844 can be disengaged to release the spring 866. The released mechanical energy causes the spring 866 to pull the outer cannula 816 in the direction of arrow 874 (FIG. 18) back to its normal, or rest, position and cutting any tissue trapped in the notches 868, 870.

It will be appreciated that the means for cutting tissue formed on the inner cannula 814 could be a sharpened edge substantially similar to the sharpened edge 342 discussed with reference to FIG. 7, without exceeding the scope of the invention. In such an embodiment, the outer cannula 816 would be extended by pushing on the outrigger portion 844 so that the notch 868 extends beyond the sharpened edge, and the tissue would be cut by the sharpened edge as the outrigger portion 844 is released.

While the preceding discussion focused on reciprocating the outer cannula relative to the inner cannula, it will be appreciated that the outer cannula can be rotated relative to the inner cannula without exceeding the scope of the invention. Rotational relative movement would cut tissue as previously described with reference to FIGS. 9 and 10.

FIG. 16 shows another embodiment of the duckbill flap valve in the form of a double duckbill valve 874 for use in the embodiments of FIGS. 14-15 and 17-18. The double duckbill valve 874 includes two domed duckbills 876 and 878. The domed duckbills 876 and 878 are formed to include circumferential flanges 880 extending axially from domed center portions 882. The duckbills 876 and 878 are operably positioned in back-to-back relation so that the flanges 880 abut each other and the domed center portions 882 cooperate to define a convex shape, as shown illustratively in FIG. 16. Each domed duckbill 876, 878 also includes a slit 884 formed in the domed center portion 882 to allow the passage of a medical instrument 750 through the double duckbill valve 874.

As in the duckbill flap valve 740 of FIGS. 14-15, the flanges 880 extend radially outwardly from the domed center portions 882 a distance equal to the thickness of the inner cannula 714. Thus, when inserted into the first channel 720, the inner cannula 714 holds the double duckbill flap valve 874 in position by pinching the flanges 880 between the proximal end of the inner cannula 714 and the shoulder 726.

Use of a double duckbill 874 provides several advantages. First, the double duckbill 874 is a two-way valve, whereas conventional duckbill valves are one-way. That is, the double duckbill 874 prevents entry of atmosphere into, as well as escape of fluids from, the body of the patient. Second, use of two identical valves in a back-to-back relation simplifies the manufacturing and assembly process and reduces inventory management requirements.

An electrocautery cutter 910 is shown in FIG. 19. Electrocautery cutter 910 includes a T-shaped conduit piece 912 interconnecting a cannula 914 and a handheld rotary valve 916. Cannula 914 is formed to include a cannula opening 918 which provides an operating site 926 for removing tissue 920 from a patient's body as shown in FIG. 20. An electrical wire 922 is connected on one end to an electrical generator 924 and on another end to cannula 914 to provide electricity to operating site 926 so that electrocautery cutter 910 can cauterize an open wound at operating site 926. An insulating sheath 928 surrounds cannula 914 and is formed to include an aperture 927 adjacent to cannula opening 918 to ensure that electricity only exits electrocautery cutter 910 at operating site 926.

Figure 22:
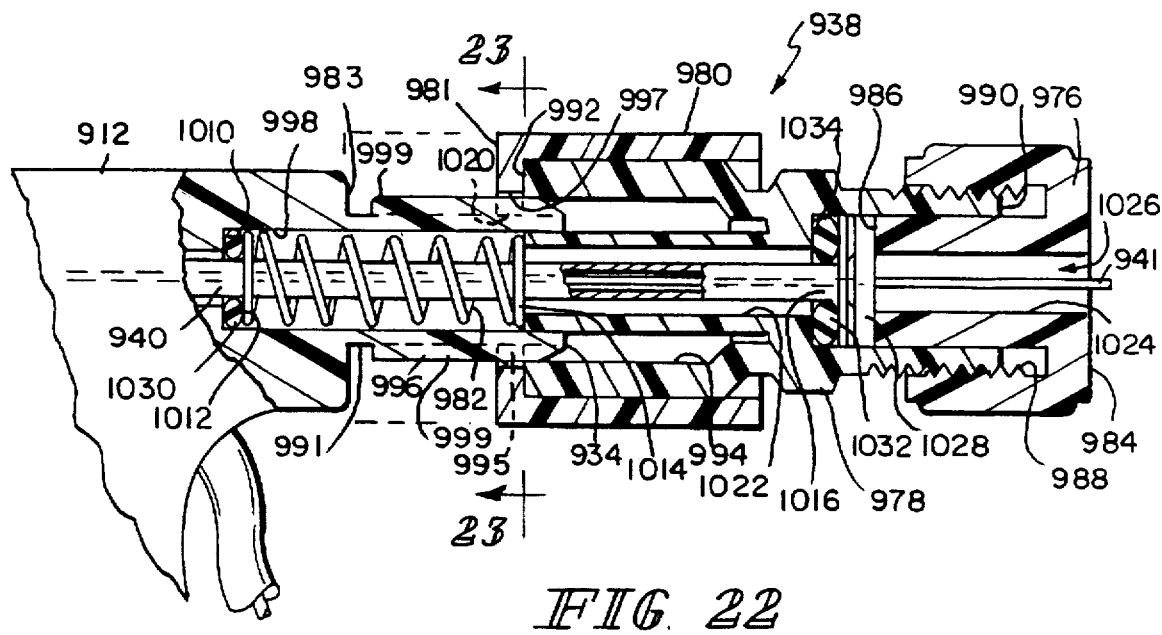
FIG. 22 is an enlarged sectional view of the cutter actuator assembly of the electrocautery cutter of FIG. 19 showing the cutter actuator assembly being spring-biased toward a non-cutting position.

Cannula 914, valve 916, and electrical wire 922 are linked together in the T-shaped conduit piece 912. T-shaped conduit piece 912 includes a first end 930 connected to valve 916, second end 932 connected to cannula 914 and insulating sheath 928, and third end 934 connected to a movable assembly or cutter actuator assembly 938. Sealing is provided to permit other medical instruments 941 such as laser vaporizers and graspers to be sealingly inserted into a tube 940 as shown in FIG. 22. Tube 940 extends from cutter actuator assembly 938 through T-shaped conduit piece 912 and into cannula 914 so that medical instrument 941 has access to a patient's body through cannula opening 918 formed in cannula 914.

A surgeon operates cutter actuator assembly 938 to move tube 940 in direction 963 from a non-cutting position to a cutting position to cut tissue 920 from a patient's body. A hollow tubular cutter 964 is appended to tube 940 to move with tube 940 in direction 963 from the non-cutting position, shown in FIGS. 19 and 20, to the cutting position. To cut tissue 920 from a patient's body, cutter actuator assembly 938 is operated by a surgeon to move cutter 964 in direction 963 until cutter 964 abuts a stationary blade or anvil 966. In the illustrated embodiment, cutter 964 has a sharpened edge 965 and anvil 966 has a sharpened edge 967. Tissue 920 is cut by the sharpened edges 965, 967 of anvil 966 and cutter 964 when cutter 964 is brought into contact with anvil 966. Cannula 914 includes a cannula side 961 that defines a cannula interior 968 and cutter 964 and anvil 966 are situated within cannula interior 968. A similar cutter 964 and anvil 966 are disclosed in U.S. patent application Ser. No. 08/333,424 to Clement, which is incorporated by reference herein. Further, any cutter assembly shown in FIGS. 1–18 may be used in the electrocautery cutter shown in FIGS. 19–23.

Tissue 920 falls into cannula interior 968 after being cut by cutter 964 and anvil 966. A suction system (not shown) is provided to draw cut tissue (not shown) through cannula interior 968 and into valve communication aperture 960 in direction 970 as shown in FIG. 19. The cut tissue then travels through valve 916 to a storage or disposal site 82, 84 as shown in FIG. 5. Valve 916 also controls aspiration and a flow of fluid through valve 916 and cannula interior 968 which is used to irrigate operating site 926. A valve actuator 917 controls the suction and irrigation functions of valve 916.

Electrocautery cutter 910 further includes a hand grip portion 942 as shown in FIG. 19. Hand grip portion 942 is formed to include an electrical wire-receiving aperture 944 through which electrical wire 922 extends.

A user grasps hand grip portion 942 with his or her hand when using electrocautery cutter 910. The flow of electricity from generator 924 to cannula opening 918 formed in cannula 914 is controlled by an electrical actuator 948 located on T-shaped conduit piece 912. Electrical actuator 948 can be adjusted by a user to open the electrical loop and not provide electrical current to cannula 914 as shown in solid electrical switch 947 or close the electrical loop to provide electrical current to cannula 914 to cauterize an open wound at operating site 926 as shown in dotted electrical switch 949 in FIG. 20. Electrical actuator 948 is a conventional device that can be a toggle type switch or a push button type switch.

The location of electrical actuator 948 permits a surgeon to use one hand to position the electrocautery cutter 910 at the operating site 926 and the fingers thereon to: operate cutter actuator assembly 938 to cut tissue 920, actuate valve actuator 917 to control suction, aspiration, and irrigation, and activate electrical actuator 948 to cauterize an open wound at operating site 926. This permits the surgeon to keep his or her other hand free to perform other duties. In alternative embodiments of the present invention, the electrical switch may be located elsewhere, such as a foot pedal (not shown).

Electrical wire 922 is linked to cannula 914 by an electrical connector 950 as shown in FIG. 19. Electrical connector 950 is a conventional device that conducts electricity from electrical wire 922 to cannula 914. In preferred embodiments of the present invention, electrical connector 950 is molded into T-shaped conduit piece 912 which is made from a plastics material. After the molding process is completed, electrical wire 922 is inserted into an electrical wire-receiving aperture 952 formed in T-shaped conduit piece 912 to engage a first end 954 of electrical connector 950 and cannula 914 is inserted into a cannula-receiving aperture 956 formed in second end 932 of T-shaped conduit piece 912 to engage a second end 958 of electrical connector 950. T-shaped conduit piece 912 is also formed to include a valve communication aperture 960 formed in first end 930 of T-shaped conduit piece 912 and a tube-receiving aperture 962 extending between second end 932 and third end 934 of T-shaped conduit piece 912. In alternative embodiments of the present invention, the hand grip portion and T-shaped conduit piece could be one integral component of the electrocautery assembly.

Cauterizing occurs when the surgeon activates electrical actuator 948 and any non-insulated portion of cannula 914 comes into contact with body tissue 920. In preferred embodiments, cannula 914 and cutter 964 are both formed of a metal and thus electrocautery current passes from cannula 914 to cutter 964. Thus, during the cutting process, cauterizing will occur when the surgeon activates electrical actuator 948 and any non-insulated portion of cutter 964 or cannula 914 (electrical cauterizing element) comes into contact with body tissue. The patient is unharmed during the cauterizing process because the patient is grounded by laying on a metal grounding plate that is connected to ground.

Cannula 914 extends from its proximal end 972 fixed in T-shaped conduit piece 912 to its distal end 974. Cannula opening 918 is formed in cannula side 961 near distal end 974 of cannula 914. Distal end 974 terminates in a tip opening or aperture 973 that allows ingress or egress of solids, liquids, or gasses from or into cannula interior 968. During the cauterizing process, the electrical current passing through cannula 914 instantly vaporizes any solids, liquids, or gasses present in cannula interior 968 without any harmful effects to the patient.

Insulation sheath 928 includes a proximal end 931 situated in cannula-receiving aperture 956 of T-shaped conduit piece 912 and a distal end 933 extending past and covering distal end 974 of cannula 914 as shown in FIGS. 19 and 20. Insulation sheath 928 includes a first diameter 975 at proximal end 931, second diameter 977 at distal end 974 of cannula 914, and a third diameter 979 at distal end 933 of insulation sheath 928. First and second diameters 975, 977 are substantially equal and third diameter 979 is less than first and second diameters 975, 977. The smaller third diameter 979 of insulation sheath 928 helps insulate distal end 974 of cannula 914. Aperture 927 is formed adjacent distal end 933 of insulation sheath 928 and cannula opening 918 formed in cannula 914. When insulation sheath 928 is situated on cannula 914, a surgeon may only cauterize at cannula opening 918 of cannula 914 because cannula opening 918 is the only non-insulated portion of cannula 914.

Figure 21:
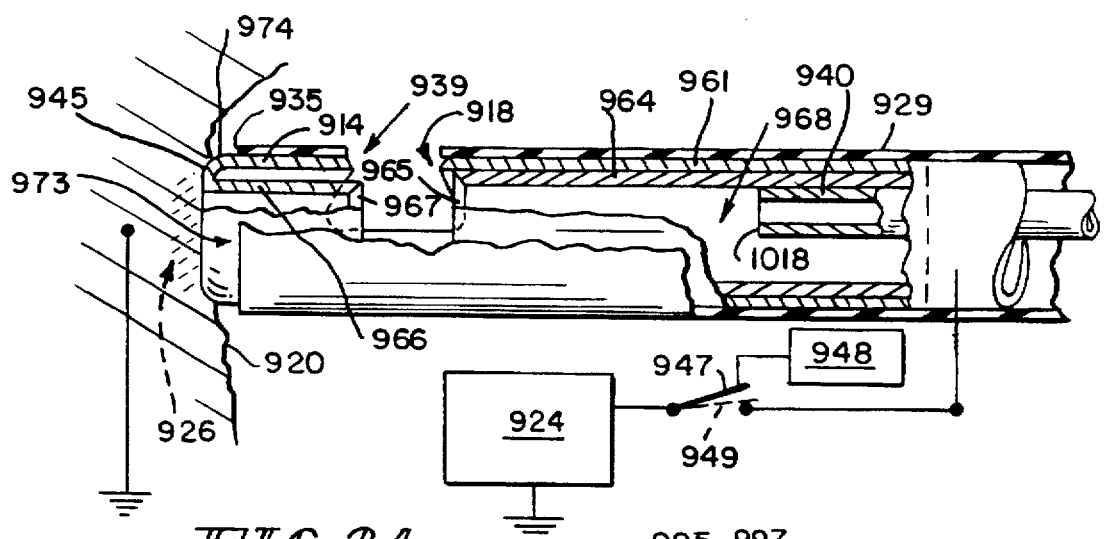
FIG. 21 is an enlarged sectional view of a portion of another preferred embodiment of the electrocautery cutter showing the distal end of the cannula extending past the insulation sheath so that a surgeon may cauterize either through the cannula opening formed in the cannula or at the distal end of the cannula.

In another preferred embodiment of the present invention, shown in FIG. 21, an insulating sheath 929 is provided to not extend past distal end 974 of cannula 914 so that distal end 974 is exposed and non-insulated. Insulation sheath 929 includes a proximal end (not shown) situated in cannula-receiving aperture 956 of T-shaped conduit piece 912 and a distal end 935 spaced apart from the proximal end (not shown) of insulation sheath 929. Insulation sheath 929 has a substantially continuous equal diameter from its proximal end (not shown) to its distal end 935. An aperture 939 is formed adjacent distal end 935 and cannula opening 918 formed in cannula 914. In this embodiment, a surgeon may cauterize either at distal end 974 of cannula 914 or at cannula opening 918 because distal end 974 and cannula opening 918 are not insulated. It is advantageous to have the capability to cauterize or coagulate at distal end 974 when tissue 920 is bleeding heavily or a vein is cut.

In the illustrated embodiments of the present invention, insulation sheathes 928, 928 are shrink wrapped onto cannula 914. In alternative embodiments, the insulation may be fixed to the cannula in any manner.

When insulation sheath 928 is shrink wrapped onto cannula 914, electrocautery cutter 910 includes a distal end 943 as shown in FIGS. 19 and 20. When insulation sheath 929 is shrink wrapped onto cannula 914, electrocautery cutter 910 includes a distal end 945 as shown in FIG. 21.

Cutter actuator assembly 938 is operated by a surgeon to move cutter 964 between the cutting and non-cutting positions. Cutter actuator assembly 938 includes a push button 976 threaded to annular projection 978, slidable with housing 980, and biased against the force of spring 982 as shown in FIG. 22. A surgeon pushes on an outer surface 984 of push button 976 to move push button 976, threaded annular projection 978, housing 980, and tube 940 against the bias of spring 982 to move cutter 964 in direction 963 from the non-cutting position to the cutting position. The surgeon can move push button 976 and thus cutter 964 in direction 963 until a first end 981 of housing 980 contacts a shoulder 983 formed adjacent third end 934 of T-shaped conduit piece 912. When the surgeon releases push button 976, spring 982 biases push button 976 and thus cutter 964 from the cutting position to the non-cutting position.

Push button 976 includes an inner end 986 and a threaded annular slot 988 formed in inner end 986. Threaded annular projection 978 includes a threaded first end 990 that extends into and mates with threaded annular slot 988 of push button 976.

Housing 980 surrounds a second end 992 of threaded annular projection 978 as shown in FIG. 22. Housing 980 and threaded annular projection 978 are formed to include a circumferentially extending guide-receiving slot 994. Third end 934 of T-shaped conduit piece 912 is formed to include a circumferentially extending guide member 996 that travels through guide-receiving slot 994 as cutter 964 travels between the cutting position and non-cutting position. Housing 980 is configured to connect to circumferentially extending guide member 996 as cutter 964 travels between the cutting position and the non-cutting position.

Figure 23:
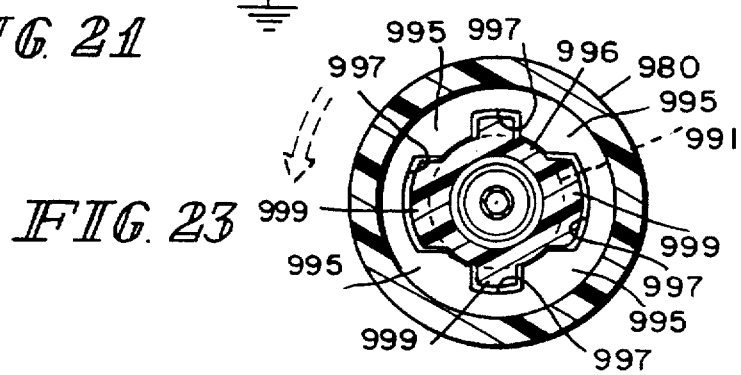
FIG. 23 is a cross-sectional view taken along line 23—23 of FIG. 22 showing spaced-apart detents formed in the cutter actuator assembly that are movable into spaced-apart detent-receiving slots (shown in phantom) to lock the cutter actuator assembly and cutter in a cutting position.

As will be explained, cutter actuator assembly 938 is configured so that a surgeon can lock cutter actuator assembly 938 and cutter 964 in a locked position by rotating cutter actuator assembly 938 approximately 90°. Push button 976 and cutter 964 can be unlocked by rotating push button 976 90° to its original position. First end 981 of housing 980 includes spaced-apart detents 995 and spaced-apart gaps 997 formed between detents 995 as shown in FIG. 23. Circumferentially extending guide member 996 is formed to include spaced-apart wings 999 and spaced-apart detent-receiving slots 991 formed between spaced-apart wings 999 and shoulder 983.

To lock cutter actuator assembly 938, cutter actuator assembly 938 is moved to its cutting position and turned until spaced-apart detents 995 are situated and trapped within detent-receiving slots 991. To unlock cutter actuator assembly 938, cutter actuator is rotated until spaced-apart detents 995 are no longer trapped within detent-receiving slots 991 and spring 982 expands to move cutter actuator assembly 938 and cutter 964 to the non-cutting position. When cutter actuator assembly 938 is unlocked, spaced-apart wings 999 of circumferentially extending guide member 996 travel through spaced-apart gaps 997 formed in housing 980 as cutter actuator assembly 938 travels between the cutting and non-cutting positions.

Third end 934 of T-shaped conduit piece 912 is formed to include a spring-receiving aperture 998 having a larger diameter than tube-receiving aperture 962 that extends from second end 932 to third end 934 of T-shaped conduit piece 912. A shoulder 1010 is formed within T-shaped conduit piece 912 between tube-receiving aperture 962 and spring-receiving aperture 998. Spring 982 includes a first end 1012 situated within spring-receiving aperture 998 and a second end 1014 abutting second end 992 of threaded annular projection 978.

Tube 940 extends from a proximal end 1016 appended to cutter actuator assembly 938 to a distal end 1018 situated within cannula interior 968 and appended to cutter 964. Housing 980, threaded annular projection 978, and push button 976 are formed to include tube-receiving apertures 1020, 1022, 1024, respectively, that form a passageway 1026 through which tube 940 and medical instruments 941 extend. Proximal end 1016 of tube 940 abuts or is appended to a tube end plate 1028. Tube end plate 1028 abuts or is appended to inner end 986 of push button 976. In alternative embodiments of the present invention, other cutter actuator assemblies such as those shown in FIGS. 1–18 can be used in the electrocautery cutter.

Sealing is provided so that medical instruments 941 can be inserted through tube 940 to acquire access to operating site 926 as shown in FIG. 20. Sealing includes first and second seals 1030, 1032 placed around tube 940. First seal 1030 is situated between first end 1012 of spring 982 and shoulder 1010 formed within third end 934 of T-shaped conduit piece 912. Second seal 1032 is situated between tube end plate 1028 and a shoulder 1034 formed in threaded annular projection 978 as shown in FIG. 22. These first and second seals 1030, 1032 prevent liquid and other matter situated within cannula 914 and valve 916 from passing out of third end 934 of T-shaped conduit piece 912 through passageway 1026.

Medical instruments 941 are inserted into an opening formed in tube end plate 1028 and through tube 940 to acquire access to operating site 926. Tube end plate 1028 includes a seal (not shown) through which the medical instruments 941 can pass into tube 940. The seal (not shown) is a conventional Touhi connector. A Touhi connector is an annular seal having a central opening that opens and closes as push button 976 threads on and off of threaded annular projection 978. In alternative embodiments of the present invention, other sealing assemblies such as those shown in FIGS. 1–18 may be used in the electrocautery cutter.

Although the invention has been described in detail with reference to certain preferred embodiments, variations and modifications exist within the scope and spirit of the invention as described and defined in the following claims.

I claim:

1. A handheld electrocautery cutter for suction, removal of body tissues and electrocauterization of tissue in a patient, the electrocautery cutter comprising:

a rigid cannula defining a cannula interior, the cannula having a proximal end and a distal end, the distal end being insertible and positionable in a patient's body, and the cannula defining a cannula opening adjacent the distal end to permit access to the cannula interior for capture of body tissue in the cannula interior;

a movable cutter for cutting tissue entering the cannula opening;

a cutter actuator configured to move the cutter, an valve connected to the cannula to control suction flow from the cannula interior;

a valve actuator configured to actuate the valve;

an electrical switch linked to the cannula to control mono-polar electrocautery current flowing from adjacent the distal end of the electrocautery cutter to the patient for cauterizing body tissue;

an electrical actuator configured to activate the electrical switch;

wherein the cannula and valve are integrated into a rigid structure to be held in a user's hand such that movement of the rigidly coupled cannula and valve by a user's hand allows the distal end of the cannula to be accurately positioned at a specific location in the patient's body; and wherein the cutter actuator, valve actuator, and electrical actuator are operable by a hand of the user as it moves the rigidly coupled valve and cannula to accurately position the distal end of the cannula in the patient's body.

2. The electrocautery cutter of claim 1, wherein the electrical actuator is integrated into the rigid structure with the cannula and valve actuator.

3. The electrocautery cutter of claim 1, wherein the rigid structure includes a hand grip portion surrounding the valve.

4. The electrocautery cutter of claim 1, wherein the cannula supports the cutter.

5. The electrocautery cutter of claim 1, wherein the cannula has an open distal end to permit communication between the cannula interior and the patient.

6. The electrocautery cutter of claim 1, wherein the valve actuator also controls irrigation through the cannula.

7. The electrocautery cutter of claim 1, wherein the mono-polar electrocautery current flows from the cutter to the patient.

8. The electrocautery cutter of claim 1, wherein the mono-polar electrocautery current flows from the distal end of the cannula to the patient for cauterizing body tissue.

9. The electrocautery cutter of claim 1, further including an insulation sheath fixed to the cannula.

10. The electrocautery cutter of claim 9, wherein the insulation sheath includes a proximal end situated in the rigid structure, a distal end spaced from the proximal end, and an aperture formed adjacent the distal end of the insulation sheath and adjacent the cannula opening formed in the cannula.

11. The electrocautery cutter of claim 10, wherein the distal end of the cannula extends past the distal end of the insulation sheath.

12. The electrocautery cutter of claim 10, wherein the distal end of the insulation sheath extends past the distal end of the cannula.

13. The electrocautery cutter of claim 1, wherein the cutter actuator is connected to the rigid structure.

14. An electrocautery cutter for suction, removal of body tissues, and electrocauterization, the electrocautery cutter comprising:

a rigid cannula defining a cannula interior, the cannula having a proximal end and a distal end, the distal end being insertible and positionable in a patient's body, and the cannula defining a cannula opening adjacent the distal end to permit access to the cannula interior for capture of body tissue in the cannula interior;

a movable cutter for cutting tissue entering the cannula opening;

a cutter actuator configured to move the cutter, an electrical switch to control mono-polar electrocautery current flowing through the cannula and from adjacent the distal end of the electrocautery cutter to the patient;

an electrical actuator configured to activate the electrical switch; and an insulation sheath being fixed to the cannula, the insulation sheath including a proximal end, a distal end spaced from the proximal end, and an aperture formed adjacent the distal end and the cannula opening formed in the cannula.

15. The electrocautery cutter of claim 14, further comprising a hand grip portion and the electrical actuator is situated adjacent the hand grip portion.

16. The electrocautery cutter of claim 15, further comprising a valve configured to extend through the hand grip portion and connect to the cannula to control suction flow from the cannula interior and a valve actuator configured to actuate the valve located adjacent the electrical actuator.

17. The electrocautery cutter of claim 14, wherein the distal end of the insulation sheath is configured to cover the distal end of the cannula.

18. The electrocautery cutter of claim 17, wherein the insulation sheath includes a first diameter at its proximal end and a second diameter at its distal end, and wherein the second diameter is smaller than the first diameter.

19. The electrocautery cutter of claim 18, wherein the insulation sheath includes a third diameter at the distal end of the cannula, and wherein the third diameter is substantially equal to the first diameter.

20. The electrocautery cutter of claim 14, wherein the distal end of the cannula extends past the distal end of the insulation sheath.

21. The electrocautery cutter of claim 14, further comprising a conduit piece and wherein the proximal end of the cannula and the proximal end of the insulation sheath are situated in the conduit.

22. The electrocautery cutter of claim 21, wherein the electrical actuator is located adjacent the conduit piece.

23. The electrocautery cutter of claim 22, further comprising a hand grip portion appended to the conduit piece and a valve means connected to the conduit piece to control suction and irrigation flow to the cannula interior and means to actuate the valve means being situated on the hand grip portion.

24. The electrocautery cutter of claim 22, further comprising a cutter actuator assembly linked to the conduit piece and configured to move the cutter between a non-cutting position and a cutting position, the cutter actuator assembly being situated so that a user can operate the electrical actuator and cutter actuator assembly with one hand.

25. The electrocautery cutter of claim 14, wherein the insulation sheath is stationary.

26. The electrocautery cutter of claim 14, wherein the cannula has an open distal end to permit communication between the cannula interior and the patient.

27. An electrocautery device comprising:

a rigid cannula having a cannula side defining a cannula interior, the cannula having a proximal end and a distal end, the distal end being insertible and positionable in a patient's body, and the cannula defining a cannula opening formed in the cannula side near the distal end to permit access to the cannula interior for capture of body tissue in the cannula interior;

an electrical switch to control mono-polar electrocautery current flowing through the cannula and from adjacent the distal end of the electrocautery cutter to the patient;

an electrical actuator configured to activate the electrical switch; and an insulation sheath covering the cannula, the insulation sheath including a proximal end, a distal end spaced from the proximal end, and an aperture formed near the distal end and adjacent the cannula opening formed in the cannula side.

28. The electrocautery device of claim 27, wherein the cannula and insulation sheath are integrated into a rigid structure to be held in a user's hand such that movement of the rigidly coupled cannula and insulation sheath by a user's hand allows the distal end of the cannula to be accurately positioned at a specific location in the patient's body, and wherein the electrical actuator is situated on the rigid structure.

29. The electrocautery device of claim 27, wherein the insulation sheath is shrink wrapped onto the cannula.

30. A handheld electrocautery cutter for suction, removal of body tissues and electrocauterization of tissue in a patient, the electrocautery cutter comprising:

a rigid cannula defining a cannula interior, the cannula having a proximal end and a distal end, the distal end being insertible and positionable in a patient's body, and the cannula defining a cannula opening adjacent the distal end to permit access to the cannula interior for capture of body tissue in the cannula interior;

a movable cutter for cutting tissue entering the cannula opening;

a cutter actuator configured to move the cutter;

a valve connected to the cannula to control suction flow from the cannula interior;

a valve actuator configured to actuate the valve;

an electrical cauterizing element connected to the cannula for introduction of mono-polar electrocautery current flowing from adjacent the distal end of the electrocautery cutter to the patient for cauterizing body tissue;

an electrical actuator for controlling the mono-polar electrocautery current flowing through the electrical cauterizing element;

wherein the cannula and valve are integrated into a rigid structure to be held in a user's hand such that movement of the rigidly coupled cannula and valve by a user's hand allows the distal end of the cannula to be accurately positioned at a specific location in the patient's body; and wherein the cutter actuator and valve actuator are operable by a hand of the user as it moves the rigidly coupled valve and cannula to accurately position the distal end of the cannula in the patient's body.

31. The electrocautery cutter of claim 30, wherein the electrical actuator is integrated into the rigid structure with the cannula and valve actuator.

32. The electrocautery cutter of claim 30, wherein the rigid structure includes a hand grip portion surrounding the valve.

33. The electrocautery cutter of claim 30, wherein the cannula supports the cutter.

34. The electrocautery cutter of claim 30, wherein the cannula has an open distal end to permit communication between the cannula interior and the patient.

35. The electrocautery cutter of claim 30, wherein the valve actuator also controls irrigation through the cannula.

36. The electrocautery cutter of claim 30, wherein the mono-polar electrocautery current flows from the distal end of the cannula to the patient for cauterizing body tissue.

37. The electrocautery cutter of claim 30, further including an insulation sheath fixed to the cannula.

38. The electrocautery cutter of claim 37, wherein the insulation sheath includes a proximal end situated in the rigid structure, a distal end spaced from the proximal end, and an aperture formed adjacent the distal end of the insulation sheath and adjacent the cannula opening formed in the cannula.

39. The electrocautery cutter of claim 38, wherein the distal end of the cannula extends past the distal end of the insulation sheath.

40. The electrocautery cutter of claim 38, wherein the distal end of the insulation sheath extends past the distal end of the cannula.

41. The electrocautery cutter of claim 30, wherein the cutter actuator is connected to the rigid structure.

\* \* \* \* \*